United States Patent
Demina et al.

(10) Patent No.: US 11,279,938 B2
(45) Date of Patent: Mar. 22, 2022

(54) DRUG DELIVERY SYSTEM AND METHODS PROVIDING THEREOF

(71) Applicant: NEUWAY Pharma GmbH, Bonn (DE)

(72) Inventors: Victoria Demina, Germany (DE); Heiko Manninga, Göttingen (DE); Sergey Sotnikov, Düsseldorf (DE); Marcus Stapf, Bonn (DE); Katja Janina Koßmann, Bonn (DE)

(73) Assignee: NEUWAY Pharma GmbH, Bonn (DE)

( * ) Notice: Subject to any disclaimer, the term of this patent is extended or adjusted under 35 U.S.C. 154(b) by 0 days.

(21) Appl. No.: 16/476,724

(22) PCT Filed: Dec. 18, 2018

(86) PCT No.: PCT/EP2018/085699
§ 371 (c)(1),
(2) Date: Jul. 9, 2019

(87) PCT Pub. No.: WO2020/125962
PCT Pub. Date: Jun. 25, 2020

(65) Prior Publication Data
US 2021/0301302 A1 Sep. 30, 2021

(51) Int. Cl.
*C07K 14/025* (2006.01)
*C12N 15/63* (2006.01)
*C12N 15/52* (2006.01)
*C07K 14/005* (2006.01)
*C12N 15/86* (2006.01)

(52) U.S. Cl.
CPC ............ *C12N 15/63* (2013.01); *C07K 14/005* (2013.01); *C12N 15/52* (2013.01); *C12N 15/86* (2013.01); *C12N 2710/22023* (2013.01); *C12N 2710/22032* (2013.01); *C12N 2710/22042* (2013.01); *C12N 2710/22051* (2013.01); *C12Y 301/06001* (2013.01)

(58) Field of Classification Search
None
See application file for complete search history.

(56) References Cited

U.S. PATENT DOCUMENTS

2005/0048047 A1 3/2005 Kakkis
2014/0309408 A1* 10/2014 Demina .................. C12N 7/00
530/413

FOREIGN PATENT DOCUMENTS

| EP | 2 636 746 A1 | 9/2013 |
|---|---|---|
| WO | 03/057179 A2 | 7/2003 |
| WO | 2013/017272 A1 | 2/2013 |
| WO | 2013/131644 A1 | 9/2013 |

OTHER PUBLICATIONS

Citkowicz et al. Characterization of virus-like particle assembly for DNA delivery using asymmetrical flow field-flow fractionation and light scattering. Analytical Biochemistry 376 (2008) 163-172.*
Daniel B. Hoffman, et al., "In Vivo siRNA Delivery Using JC Virus-like Particles Decreases the Expression of RANKL in Rats", Molecular Therapy-Nucleic Acids, Jan. 1, 2016, pp. 1-10.
Claudia Goldmann, et al., "Packaging of small molecules into VP1-virus-like particles of the human polyomavirus JC virus", Journal of Virological Methods, Oct. 1, 2000, pp. 85-90, vol. 90, No. 1.
Andrzej Citkowicz, et al., "Characterization of virus-like particle assembly for DNA delivery using asymmetrical flow field-flow fractionation and light scattering", Analytical Biochemistry, May 15, 2008, pp. 163-172, vol. 376, No. 2.
International Search Report for PCT/EP2018/085699 dated Jun. 4, 2019 [PCT/ISA/210].
Written Opinion for PCT/EP2018/085699 dated Jun. 4, 2019 [PCT/ISA/237].
Maribel Cayetano-Cruz, et al., "Decoration of virus-like particles with an enzymatic activity of biomedical interest", Virus Research, Aug. 1, 2018, vol. 255, pp. 1-9 (9 pages total).
Noriko Miyake, et al., "Successful Treatment of Adult MLD Model Mice By Intravenous Injection of Self-Complementary Type 9 AAV Vector Expressing ASA", Molecular Therapy, Supplement 1, May 1, 2014, vol. 22, pp. S151-S151 (1 page total).
International Search Report in International Application No. PCT/EP2019/060814, dated Jul. 9, 2019.

* cited by examiner

*Primary Examiner* — Nianxiang Zou
(74) *Attorney, Agent, or Firm* — Sughrue Mion, PLLC

(57) ABSTRACT

The invention relates to a method for providing a drug delivery system, in particular for crossing the blood brain barrier (BBB), comprising a virus-like particle (VLP) derived from John Cunningham virus (JCV), a drug delivery system and novel VLP obtainable by said method. The method comprises steps of disassembly of VLP into pentamers and reassembly into VLP.

37 Claims, 9 Drawing Sheets
Specification includes a Sequence Listing.

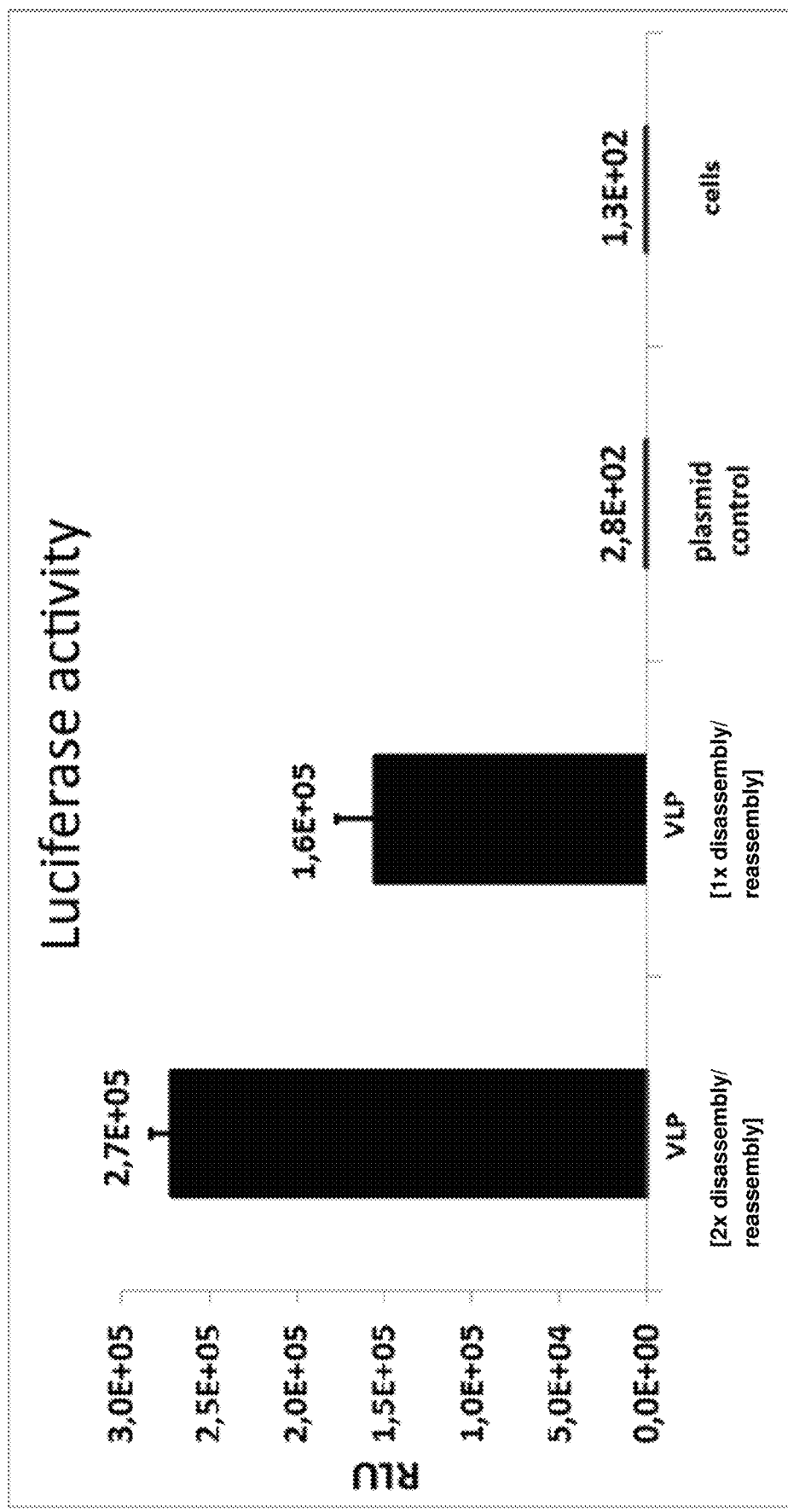

Fig. 4
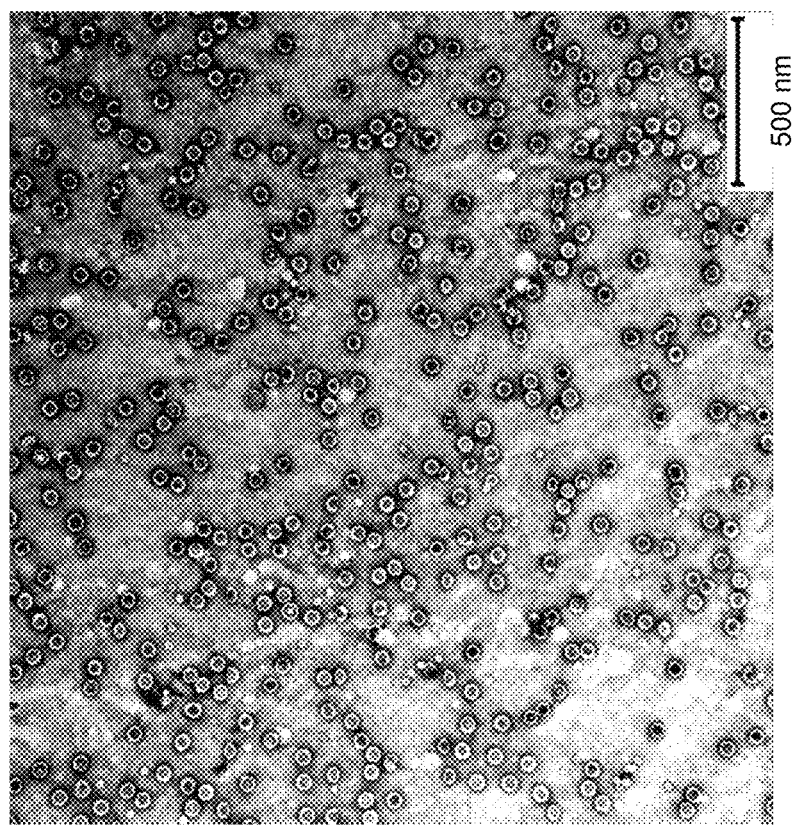
VLP (2x diassembled/reassembled – intermediate VLP frozen)
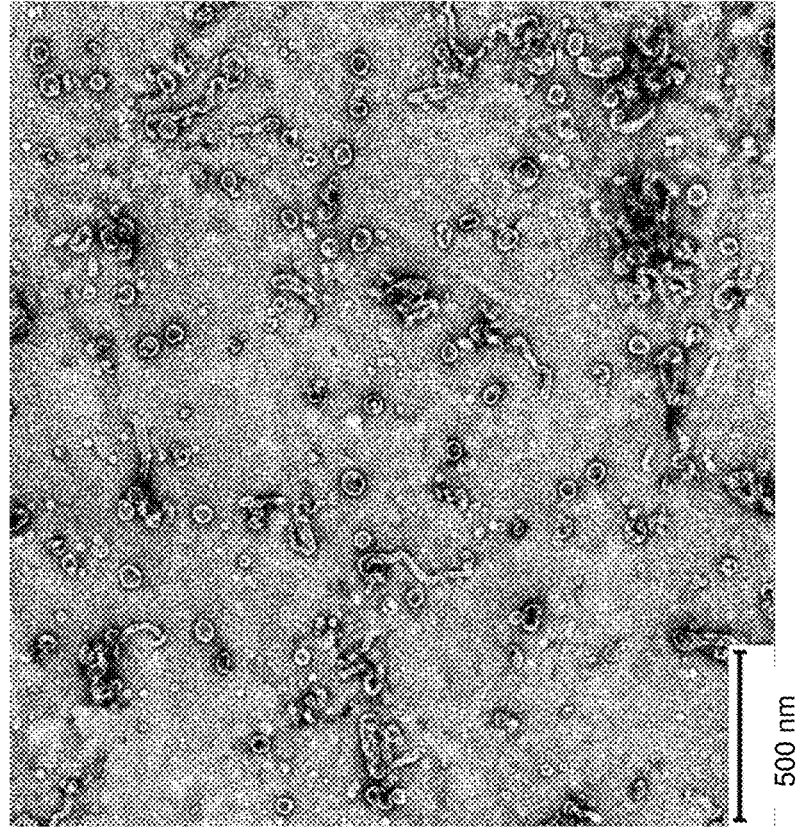
VLP (1x disassembled/reassembled - intermediate pentamers frozen)

SEQUENCE LISTING

```
<160> NUMBER OF SEQ ID NOS: 4

<210> SEQ ID NO 1
<211> LENGTH: 354
<212> TYPE: PRT
<213> ORGANISM: Artificial Sequence
<220> FEATURE:
<223> OTHER INFORMATION: Synthetic sequence, derived from JC virus

<400> SEQUENCE: 1

Met Ala Pro Thr Lys Arg Lys Gly Glu Pro Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
```

```
                50                  55                  60
Ser Asp Thr Phe Glu Ser Asp Ser Pro Asn Arg Asp Met Leu Pro Cys
 65                  70                  75                  80

Tyr Ser Val Ala Arg Ile Pro Leu Pro Asn Leu Asn Glu Asp Leu Thr
                 85                  90                  95

Cys Gly Asn Ile Leu Met Trp Glu Ala Val Thr Leu Lys Thr Glu Val
                100                 105                 110

Ile Gly Val Thr Ser Leu Met Asn Val His Ser Asn Gly Gln Ala Thr
                115                 120                 125

His Asp Asn Gly Ala Gly Lys Pro Val Gln Gly Thr Ser Phe His Phe
130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
                180                 185                 190

Asn Lys Ala Tyr Pro Val Glu Cys Trp Val Pro Asp Pro Thr Arg Asn
                195                 200                 205

Glu Asn Thr Arg Tyr Phe Gly Thr Leu Thr Gly Gly Glu Asn Val Pro
210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
                260                 265                 270

Arg Gly Leu Ser Arg Tyr Phe Lys Val Gln Leu Arg Lys Arg Arg Val
                275                 280                 285

Lys Asn Pro Tyr Pro Ile Ser Phe Leu Leu Thr Asp Leu Ile Asn Arg
                290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Lys Tyr Gly Gln Leu Gln Thr Lys
                340                 345                 350

Met Leu

<210> SEQ ID NO 2
<211> LENGTH: 1065
<212> TYPE: DNA
<213> ORGANISM: Artificial Sequence
<220> FEATURE:
<223> OTHER INFORMATION: Synthetic sequence, derived from JC virus

<400> SEQUENCE: 2
atggctccca ccaagcgcaa gggcgagccc aaggaccccg tgcaagtgcc caagctgctg      60
atccgtggtg gtgtcgaggt gctggaagtc aagaccggcg tggactccat taccgaggtg     120
gagtgcttcc tcaccccccga gatgggtgac cctgacgagc acctgagggg cttctccaag    180
tccatctcca tctccgacac cttcgagtcc gactccccca accgtgacat gctgccctgc     240
tactccgtgg ctcgtatccc cctgcccaac ctgaacgagg acctgacttg cggcaacatc     300
ctgatgtggg aggctgtgac cctcaagacc gaggtcatcg gcgtgacttc cctgatgaac     360
```

```
gtgcactcca acggccaggc tacccacgac aacggtgctg gcaagcccgt gcagggaacc    420
tccttccact tcttctccgt gggtggcgag gctctggaac tccagggcgt ggtgttcaac    480
taccgtacca agtaccccga cggcaccatc ttccccaaga acgctactgt gcagtcccaa    540
gtgatgaaca ccgagcacaa ggcttacctg acaagaaca aggcctaccc cgtggagtgc    600
tgggtgcccg accccacccg taacgagaac accgttact tcggcaccct gaccggtgga    660
gagaacgtgc ccccgtgct gcacatcacc aacaccgcta ccaccgtgct gctggacgag    720
ttcggtgtcg gtccctgtg caagggcgac aacctgtacc tgtccgctgt ggacgtgtgc    780
ggcatgttca ccaaccgttc cggttcccag cagtggcgtg gcctgtcccg ctacttcaag    840
gtgcagctgc gcaagcgtcg tgtgaagaac ccctaccta tctccttcct gctgaccgac    900
ctgatcaacc gtcgtacccc tcgtgtggac ggccagccca tgtacggcat ggacgctcag    960
gtggaagagg tccgcgtgtt cgagggcacc gaggaattgc ccggcgaccc cgacatgatg    1020
cgttacgtgg acaagtacgg ccagctccag accaagatgc tgtaa                   1065
```

<210> SEQ ID NO 3
<211> LENGTH: 354
<212> TYPE: PRT
<213> ORGANISM: JC virus

<400> SEQUENCE: 3

```
Met Ala Pro Thr Lys Arg Lys Gly Glu Arg Lys Asp Pro Val Gln Val
1               5                  10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Ser Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Ser Leu Met Asn Val His Ser Asn Gly Gln Ala Ala
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
```

```
                        245                 250                 255
Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Val
            275                 280                 285

Lys Asn Pro Tyr Pro Ile Ser Phe Leu Leu Thr Asp Leu Ile Asn Arg
            290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
            325                 330                 335

Pro Asp Met Met Arg Tyr Val Asp Arg Tyr Gly Gln Leu Gln Thr Lys
            340                 345                 350

Met Leu

<210> SEQ ID NO 4
<211> LENGTH: 1065
<212> TYPE: DNA
<213> ORGANISM: JC virus

<400> SEQUENCE: 4
atggccccaa caaaagaaa aggagaaagg aaggacccccg tgcaagttcc aaaacttctt    60
ataagaggag gagtagaagt tctagaagtt aaaactgggg ttgactcaat tacagaggta   120
gaatgctttt taactccaga aatgggtgac ccagatgagc atcttagggg ttttagtaag   180
tcaatatcta tatcagatac atttgaaagt gactccccaa ataggacat gcttccttgt   240
tacagtgtgg ccagaattcc actacccaat ctaaatgagg atctaacctg tggaaatata   300
ctcatgtggg aggctgtgac cttaaaaact gaggttatag gggtgacaag tttgatgaat   360
gtgcactcta atgggcaagc aactcatgac aatggtgcag ggaagccagt gcagggcacc   420
agctttcatt tttttctgt tggggggag gcttagaat tacaggggt gcttttaat      480
tacagaacaa agtacccaga tggaacaatt tttccaaaga atgccacagt gcaatctcaa   540
gtcatgaaca cagagcacaa ggcgtaccta gataagaaca aagcatatcc tgttgaatgt   600
tgggttcctg atcccaccag aaatgaaaac acaagatatt ttgggacact aacaggagga   660
gaaaatgttc ctccagttct tcatataaca aacactgcca caactgttt gcttgatgaa   720
tttggtgttg ggccactttg caaaggtgac aacttatact tgtcagctgt tgatgtctgt   780
ggcatgttta caaacaggtc tggttcccag cagtggagag gactctccag atattttaag   840
gtgcagctaa ggaaaaggag ggttaaaaac ccctacccaa tttctttcct tcttactgat   900
ttaattaaca gaaggactcc tagagttgat gggcagccta tgtatggcat ggatgctcaa   960
gtagaggagg ttagagtttt tgagggaaca gaggagcttc cagggggaccc agacatgatg  1020
agatacgttg acaaatatgg acagttgcag acaaaaatgc tgtaa                  1065
```

DRUG DELIVERY SYSTEM AND METHODS PROVIDING THEREOF

CROSS REFERENCE TO RELATED APPLICATIONS

This application is a National Stage of International Application No. PCT/EP2018/085699 filed Dec. 18, 2018.

FIELD OF THE INVENTION

The invention relates to a method for providing a drug delivery system (DDS), in particular for crossing the blood brain barrier (BBB), comprising a virus-like particle (VLP) derived from John Cunningham virus (JCV), a drug delivery system and novel VLP and VLP containing compositions obtainable by said method.

BACKGROUND OF THE INVENTION

The blood brain barrier (BBB) is a highly selective and permeable membrane between blood and the brain. The barrier functions to separate the circulating blood from the brain extracellular fluid (BECF) in the central nervous system (CNS). The BBB is highly selective in nature and allows, by passive diffusion, only the passage of lipid soluble molecules, water and certain gases. The barrier also selectively transports molecules, such as glucose and amino acids, which are essential for neural functions. In addition, the BBB hinders the entry of lipophilic potential neurotoxins into the brain.

Under physiological conditions the BBB functions effectively to substantially prevent unwanted material from entering the CNS. Large nano-therapeutics and the vast majority of small molecules (estimated are 98% of the small molecules) are restricted to enter into the brain because of the BBB. Under physiological (healthy) conditions, the function of the BBB is therefore invaluable. In the event of a CNS disease or any other disorder which requires the treatment of the CNS with a pharmaceutical product, however, the BBB constitutes a major hurdle to an effective treatment.

In addition to the problem of successfully transferring the pharmaceutical product (drug, cargo) across the BBB, heed has to be paid to those problems, which can be encountered during CNS delivery. Even if the pharmaceutical product crosses the BBB, it may not be present in a therapeutically relevant concentration. Moreover, certain enzymes in the brain tissue can inactivate the pharmaceutical product, rendering it ineffective or less effective. Thus, the pharmaceutical product may be able to cross the BBB, but can be deconstructed once it is inside the brain.

Several strategies are known for affecting a transport of a pharmaceutical product across the BBB. The extent to which a pharmaceutical product indeed is able to penetrate into the brain varies from one strategy to the other. One strategy is to increase the permeability of the BBB. Therewith not only the amount of the pharmaceutical product that crosses the BBB may be increased, but both the free and bound forms of the pharmaceutical product can be made to cross the barrier.

Means for increasing the permeability of the BBB include an osmotic opening or chemical opening. Osmotic opening might be possible with hypertonics, which have the capability of disrupting BBB when applied directly onto its surface. Chemical opening is a more selective and controllable approach of increasing the permeability of BBB. Normal capillaries appear to be unaffected when vasoactive leukotriene treatments are used to increase their permeability. Brain tumor capillaries are more sensitive to these treatments. Studies have revealed that bradykinin opens the brain tumor capillaries without affecting the capillaries in the normal brain.

Cerebral vasodilatation or focused ultrasound radiation represent other approaches for increasing the permeability of the BBB. Cerebral vasodilatation refers to the process of widening of blood vessels to increase cerebral blood flow. Focused ultrasound radiation, namely low frequency (e.g. 260 kHz), MRI-guided ultrasound can induce localized and reversible disruption of the barrier.

Another approach of transporting a pharmaceutical product into the CNS is the use of a drug delivery system on the basis of virus-like particles (VLP) derived from John Cunningham virus (JCV). The VLP are loaded with a drug ("cargo"). Such a drug delivery system is disclosed in WO 2013/131644 A1. It is described that, after intravenous administration, the VLP can cross the BBB without a prior manipulation thereof, therewith transporting the drug together with the VLP over a physiologically intact BBB. A method for the production of a drug delivery system comprising VLP from JCV is subject matter of WO 2013/017272 A1.

The disclosure of the WO 2013/131644 A1 provided the first experimental evidence of the crossing of a VLP from JCV over the physiological intact BBB in vivo. Hence VLP from JCV loaded with a pharmaceutical product are promising drug delivery systems for entering the CNS. However, there is still a need to further improve the efficacy of this system.

SUMMARY OF THE INVENTION

It is thus an objective of the present invention to provide a drug delivery system on the basis of VLP derived from John Cunningham virus (JCV), in particular for the delivery of a pharmaceutical product into the CNS, which has an improved efficacy. An improved efficacy in particular means that more cargo reaches the CNS. The improved efficacy can have manifold reasons, which might interact. The higher efficacy can for example be due to a more efficacious crossing of the BBB by the VLP, so that a higher amount of VLP and/or cargo enters the CNS. It can equally be due an improved release of the cargo from the VLP after reaching the CNS. Furthermore, a reason for the higher efficacy can be the fact that each individual VLP can be loaded with a higher amount of cargo or the overall amount of loaded VLP can be increased.

It was surprisingly found by the inventors that a drug delivery system comprising VLP derived from JCV with an improved efficacy can be provided, when the method for the production of said drug delivery system comprises twice the steps of disassembling the VLP into pentamers and reassembling the pentamers into a VLP. The method comprises the following steps a) providing a composition comprising VP1 proteins of JCV,
b) exposing the VP1 proteins of the composition of a) to conditions inducing the VP1 to assemble into VLP,
c) exposing the VLP of the composition of b) to conditions disassembling the VLP into pentamers,
d) exposing the pentamers of the composition of c) to conditions inducing the pentamers to reassemble into VLP,
e) exposing the VLP of the composition of d) to conditions disassembling the VLP into pentamers, f) exposing the pentamers of the composition of e) to a cargo and conditions inducing the pentamers to assemble into VLP associated with the cargo.

The improved efficacy of the drug delivery system obtainable by the method according to the invention is demonstrated by the increased expression of luciferase, when the cargo of the drug delivery system is the luciferase expression plasmid NanoLuc® (Example 1 below, FIG. 1). Therewith, additionally, the suitability of the drug delivery system of the invention for the delivery of nucleic acids as cargo is shown.

Example 1 furthermore gives evidence that the VLP obtained in step f) efficiently cross the BBB (Example 1 below, FIGS. 2 and 3). Therewith, evidence is provided, that the VLP can be used as a drug delivery system for the transport of a drug into the CNS.

Moreover, it has been found, that the VLP obtained in step d), are particularly suitable for storage. They withhold storage conditions of −80° C. for a period of more than 24 h. After storage the VLP can be further processed for providing the drug delivery system.

Hence they represent a suitable storeable intermediate product during the manufacture of a drug delivery system comprising VLP associated with a cargo.

In one particular aspect, thus, the invention relates to a method for providing VLP with an increased suitability for storage. Such VLP, for practical reasons, substantially facilitate the production of the drug delivery system. It allows for the large-scale manufacture of VLP and, then, their intermediate storage without cargo. After storage, on demand of the individual costumer, the stored VLP can be further processed and loaded with the desired cargo. Therefore, the intermediate storage of the VLP provided in step d) enables more flexibility in the manufacturing process of a drug delivery system on the basis of VLP.

Furthermore, it has been found that the VLP according to the invention are stable. Their stability can be equally compared with the VLP which are the result from VP1 production and a direct subsequent assembly, i.e. without a disassembly/reassembly step (FIG. 6). Therefrom it follows, that the two disassembly and reassembly steps according to the invention, surprisingly, do not have a negative impact on the stability of the VLP.

In yet another aspect, the invention relates to a drug delivery system or a composition comprising VLP.

It was further surprisingly found, that the homogeneity of the composition comprising VLP can be improved by reassembling the pentamers of step d) in two steps, whereas the first step comprises inducing the aggregation of the pentamers of step c) and the second step comprises separating the pentamers from the conditions inducing the aggregation of the pentamers (Example 3 below, FIGS. 7 and 8).

A homogeneous size distribution of the composition comprising VLP is advantageous because it allows producing a defined population of VLP for use as the drug delivery system which is important to fulfill a defined quality standard.

BRIEF DESCRIPTION OF THE FIGURES

FIG. 1 Luciferase activity measured in glioblastoma cells transfected either with VLP prepared according to the invention (two rounds of disassembly and reassembly) or with VLP having been disassembled and reassembled only once (prior art)

DETAILED DESCRIPTION OF THE INVENTION

Figure 2A:
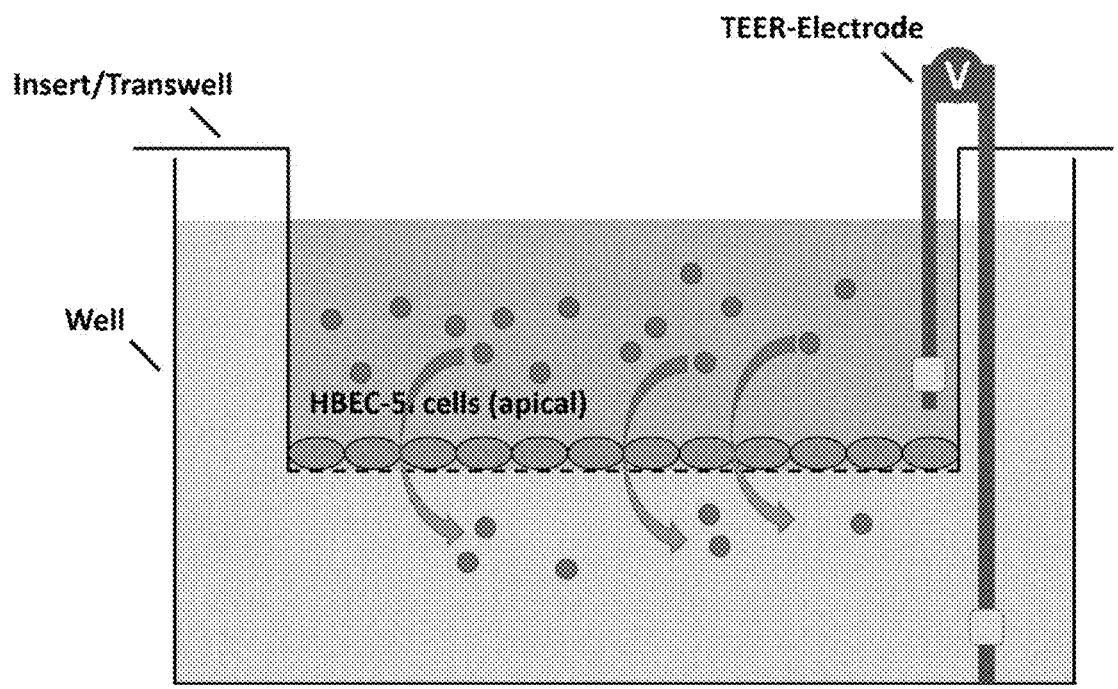
FIG. 2 Setup (A) of a BBB model as a monoculture and permeability (B) of VLP prepared according to the invention FIG. 3 Setup (A) of a BBB model as a coculture and permeability (B) of VLP prepared according to the invention FIG. 4 TEM images of VLP according to the invention (after two rounds of disassembly/reassembly) versus VLP of the prior art (after one round of disassembly and reassembly), and with intermediate storage FIGS. 5A-5C FFF-MALS analyses of VLP according to the invention (after two rounds of disassembly and reassembly) with intermediate storage of the VLP FIG. 5A), VLP with one round of disassembly and reassembly with intermediate storage of the pentamers (FIG. 5B) and freshly prepared VLP (FIG. 5C).

In a first aspect of the invention, the invention relates to a method for providing a drug delivery system comprising a virus-like particle (VLP) derived from John Cunningham virus (JCV) comprising the following steps:
  a) providing a composition comprising VP1 proteins,
  b) exposing the VP1 proteins of the composition of a) to conditions inducing the VP1 to assemble into VLP,
  c) exposing the VLP of the composition of b) to conditions disassembling the VLP into pentamers,
  d) exposing the pentamers of the composition of c) to conditions inducing the pentamers to reassemble into VLP
  e) exposing the VLP of the composition of d) to conditions disassembling the VLP into pentamers,
  f) exposing the pentamers of the composition of e) to a cargo and conditions inducing the pentamers to assemble into VLP associated with the cargo.

In the context of the present invention, and for the ease of explanation, the VLP resulting from step b) may also be termed "pVLP" (primary VLP). The VLP resulting from step d) may also be termed "rVLP" (reassembled VLP). The VLP as the result of step f) may also be termed "cVLP" (cargoVLP).

In a second aspect of the invention, the invention relates to a composition comprising virus-like particles (VLP) derived from John Cunningham virus (JCV) characterized by one or more of the following parameters:
  a. a polydispersity index (PDI) of less than 0.3, preferably less than 0.2, preferably less than 0.1, more preferably in a range between 0.01 and 0.09,
  b. at least 70% of VLP with an average diameter from 20 nm to 70 nm, preferably of 30 nm to 70 nm, more preferably of 35 nm to 65 nm, more preferably of 40 to 60 nm,
  c. a VLP content within the composition of at least 80% (v/v), preferably at least 85% (v/v), preferably at least 90% (v/v), preferably at least 95% (v/v).

In a third aspect, the invention relates to a drug delivery system obtainable by the method according to the invention.

The drug delivery system can be used in a method of therapy and/or diagnosis, preferably for the treatment of neurological disorders. Hence the invention also relates to a method of treatment of a disorder, in particular a CNS disease, with the drug delivery system according to the invention. The method of treatment preferably comprises the step of administering the drug delivery system to a subject in need thereof.

The drug delivery system preferably has an improved efficacy. The VLP can cross the BBB without a prior tially remain intact, preferably they essentially maintain their capsid structure. If loaded with cargo, they essentially remain associated with the cargo. It is especially suitable as a pharmaceutical composition for the intravenous administration of the VLP to a subject, in particular to a human.

In yet a further aspect of the invention a composition comprising VLP is provided, which has least one, preferably all, of the following characteristics ("target parameters"):

TABLE 1

Preferred characteristics of the VLP and the VLP-containing composition.

| Methods for evaluation | Measurement | Target Parameters |
| --- | --- | --- |
| Transmission Electron Microscopy (TEM) | VLP per grid mesh | >50 particles |
| | Shape of particles | round and enclosing |
| | Diameter of particles | 40-50 nm |
| | Aggregates | Not visible |
| SDS PAGE and Western Blot (WB) | VP1 band | 40 kDa band is observed |
| | VP1 degradation | Minor or no degradation |
| Dynamic Light Scattering (DLS) | PDI | <0.2 |
| | Single peak (volume based distribution) | Yes |
| | Z-average diameter | 40-50 nm |
| | Other peaks (volume based distribution) | Not detectable |
| Bioanalyzer | VP1 purity (40 kDa) | >90% |
| Thermal Shift Assay (TSA) | Major melting peak (in Tris-HCl-Buffer) | >57° C. |
| | Minor melting peaks | Not detectable |
| Nano Differential Scanning Fluorometry (nDSF) | Major inflection peak | >69° C. |
| | Minor inflection peaks | Not detectable |
| Size Exclusion HPLC (SE-HPLC) | Aggregates | <5% of total AUC |
| | Other impurities | <5% of total AUC |
| Field Flow Fractionation (FFF-MALS) | Concentration of particles | >1.0 × $10^{11}$ VLP/mL |
| | Size of particles | 40-50 nm |
| | Aggregates | <5% of total AUC |
| | Other impurities | <5% of total AUC |

AUC = area under the curve increase of the permeability of the BBB. Hence, the drug delivery system of the invention can be used in a method of treatment of a CNS disease, wherein the method does not comprise a step of increasing the permeability of the BBB of the subject to be treated. The drug delivery system of the invention, preferably, is administered to a patient who has not received any chemical or physical treatment for impairing or disrupting the BBB.

In a fourth aspect of the invention, the invention relates to a virus-like particles (VLP) derived from John Cunningham virus (JCV) obtainable by a method comprising steps a) to e) of the method of the invention and a further step of exposing the pentamers of the composition of e) to conditions inducing the pentamers to assemble into VLP. These VLP are cargo-free. They are particularly useful as a vaccine.

In a fifth aspect of the invention, a composition is provided which comprises virus-like particles (VLP) derived from John Cunningham virus (JCV) comprising a salt and a buffer and having a pH between 7.0 and 8.0, preferably around 7.5. The composition preferably comprises:
  a. 120 mM to 170 mM NaCl, preferably 150 mM NaCl,
  b. 1 to 5 mM CaCl$_2$, preferably 2 mM CaCl$_2$, and
  c. 5 to 30 mM Tris-HCl, preferably 10 to 25 mM Tris-HCl, more preferably 10 mM Tris-HCl.

This composition allows handling the VLP under physiological conditions. Under these conditions the VLP essen- In the context of the invention, the term "drug delivery system" refers to a composition for administering a pharmaceutical product to a subject in the need thereof, in particular to a human or animal. A drug delivery system, advantageously, enables the delivery of the pharmaceutical product contained therein or attached thereto to a site of interest, preferably in a human or animal. Preferably the delivery is selective for the target, i.e. more of the pharmaceutical product is delivered to the target than to other sites of the body or organ.

"A drug delivery system for the CNS" means that the drug delivery system selectively targets the CNS. CNS refers to the spinal cord and the brain, in particular to the brain. The term "brain" includes anatomical parts thereof, such as frontal lobe, parietal lobe, temporal lobe, occipital lobe, and cerebellum.

The drug delivery system of the invention can be administered via various routes, including oral, dermal, nasal or pulmonary routes or injection. Particularly preferred are dosage forms which allow a systemic effect of the pharmaceutical product. In a specific embodiment the drug delivery system of the invention is administered orally or parenterally, in particular intravenously.

The drug delivery system of the present invention comprises a virus-like particle (VLP) derived from John Cunningham virus (JCV). The "JC virus" or John Cunningham virus (JCV; NCBI Taxonomy 10632) is a human polyomavirus. JCV is of an icosahedral symmetry, has a diameter of about 45 nm and consists of 72 VP1 pentamers. Small numbers of the structural proteins VP2 and VP3 are also present.

A "virus-like particle" (VLP) in the context of the present invention is defined as a replication-deficient particle with a hull (also termed capsid) composed of viral structural proteins or modified viral structural proteins or proteins derived from viral structural proteins. The VLP according to the invention is derived from JCV, i.e. its hull is composed of viral structural proteins or modified viral structural proteins or proteins derived from viral structural proteins VP1, VP2 and VP3 from JCV, in particular from VP1.

In a particularly preferred embodiment of the invention the only viral structural protein in the hull is a VP1 protein. In the most preferred embodiment the hull of the VLP consists of VP1 proteins, i.e. the hull does not contain any other protein.

The viral structural proteins, in particular the VP1, assemble into pentameric structures (pentamers). According to the invention, the VLP hull preferably is composed of several VP1 proteins, in particular several VP1 pentamers, especially 72 VP1 pentamers.

A "pentamer" in the context of the invention is a structure which is formed when five polypeptides, for example VP1 proteins, assemble. The assembly into a pentamer may be due to the formation of covalent or non-covalent bonds between the polypeptides. The polypeptides typically form a ring-shaped structure, having pentagonal symmetry. In a pentamer, each polypeptide subunit preferably interacts with two adjacent subunits.

A "peptide" according to the present invention may be composed of any number of amino acids of any type, preferably naturally occurring amino acids, which preferably are linked by peptide bonds. In particular, a peptide comprises at least 3 amino acids, preferably at least 5, at least 7, at least 9, at least 12 or at least 15 amino acids. There is no upper limit for the length of a peptide. However, preferably a peptide according to the invention does not exceed a length of 500 amino acids, preferably 400, 300, 250, 200, 150 or 120 amino acids. A peptide exceeding about 10 amino acids may also be termed a "polypeptide".

The structural proteins of the VLP, in particular the VP1, are identical to or derived from the native structural proteins of JCV. "Modified or derived" encompasses the insertion, deletion or substitution of one or more amino acids while retaining the function of VP1 to assemble into a capsid.

In one embodiment, the native (JCV) structural protein can be modified in order to optimize the VLP with regard to its production, its cellular targeting profile and specificity or its intracellular targeting profile or specificity. Modification or derivation can comprise a codon optimization of the nucleotide sequence encoding the structural protein, in particular the VP1, to enhance protein translation.

The terms "VP1" or "virus protein 1" according to the present invention refer to a protein which is identical to or is derived from the natural VP1 of the JCV and which is capable of assembling into a capsid.

The term "VP1" according to the invention encompasses a protein which has an amino acid sequence identity with the amino acid sequence according to SEQ ID NO: 1 of at least 80%, more preferably at least 85%, more preferably at least 90%, more preferably at least 95%, more preferably at least 97%, more preferably at least 98% or at least 99% over this sequence. In a most preferred embodiment of the invention the VP1 has the amino acid sequence according to SEQ ID NO: 1.

The term "VP1" according to the invention also encompasses fractions of the native VP1. Preferably, said fractions of VP1 comprise at least acids 32 to 316 of the amino acid sequence according to SEQ ID NO: 1 or a derivative thereof having an identity with the amino acid sequence from amino acid position 32 to 316 of SEQ ID NO: 1 of at least 80%, more preferably at least 85%, more preferably at least 90%, more preferably at least 95%, more preferably at least 97%, more preferably at least 98% or at least 99% over this sequence.

In a preferred embodiment of the invention the VP1 has an amino acid sequence which is at least 80%, more preferably at least 85%, more preferably at least 90%, more preferably at least 95%, more preferably at least 99% identical to the amino acid sequence according to SEQ ID NO: 1 over its entire length. In a most preferred embodiment of the invention, the VP1 has an amino acid sequence which is identical to the amino acid sequence according to SEQ ID NO: 1.

In another embodiment of the invention the VP1 has an amino acid sequence which is at least 80%, more preferably at least 85%, more preferably at least 90%, more preferably at least 95%, more preferably at least 99% identical to the amino acid sequence according to SEQ ID NO: 3 over its entire length. In one embodiment, the amino acid sequence of VP1 is identical to the amino acid sequence of SEQ ID NO: 3.

In one embodiment, the nucleotide sequence of the VP1 protein is at least 70%, more preferably at least 80%, more preferably at least 90% identical to the nucleotide sequence of SEQ ID NO: 2 over its entire length, preferably is the nucleotide sequence of SEQ ID NO: 2.

In another embodiment of the invention the nucleotide sequence of the VP1 protein is at least 70%, more preferably at least 80%, more preferably at least 90% identical to the nucleotide sequence of SEQ ID NO: 4 over its entire length. In one embodiment, the nucleotide sequence of the VP1 protein is identical to the nucleotide sequence of SEQ ID NO: 4.

The sequences are depicted in Table 2.

TABLE 2

| Amino acid and nucleotide sequences of the VP1 protein. | | | |
|---|---|---|---|
| Protein/DNA | Sequence | Source | SEQ ID NO: |
| Protein | MAPTKRKGEPKDPVQVPKLLI RGGVEVLEVKTGVDSITEVEC FLTPEMGDPDEHLRGFSKSIS ISDTFESDSPNRDMLPCYSVA RIPLPNLNEDLTCGNILMWEA VTLKTEVIGVTSLMNVHSNGQ ATHDNGAGKPVQGTSFHFFS VGGEALELQGVVFNYRTKYP DGTIFPKNATVQSQVMNTEH | derived from JCV | 1 |

TABLE 2-continued

Amino acid and nucleotide sequences of the VP1 protein.

| Protein/DNA | Sequence | Source | SEQ ID NO: |
|---|---|---|---|
| | KAYLDKNKAYPVECWVPDPT RNENTRYFGTLTGGENVPPV LHITNTATTVLLDEFGVGPLCK GDNLYLSAVDVCGMFTNRSG SQQWRGLSRYFKVQLRKRR VKNPYPISFLLTDLINRRTPRV DGQPMYGMDAQVEEVRVFE GTEELPGDPDMMRYVDKYG QLQTKML | | |
| DNA | ATGGCTCCCACCAAGCGCA AGGGCGAGCCCAAGGACCC CGTGCAAGTGCCCAAGCTG CTGATCCGTGGTGGTGTCG AGGTGCTGGAAGTCAAGAC CGGCGTGGACTCCATTACC GAGGTGGAGTGCTTCCTCA CCCCCGAGATGGGTGACCC TGACGAGCACCTGAGGGGC TTCTCCAAGTCCATCTCCAT CTCCGACACCTTCGAGTCC GACTCCCCCAACCGTGACAT GCTGCCCTGCTACTCCGTG GCTCGTATCCCCCTGCCCAA CCTGAACGAGGACCTGACTT GCGGCAACATCCTGATGTG GGAGGCTGTGACCCTCAAG ACCGAGGTCATCGGCGTGA CTTCCCTGATGAACGTGCAC TCCAACGGCCAGGCTACCC ACGACAACGGTGCTGGCAA GCCCGTGCAGGGAACCTCC TTCCACTTCTTCTCCGTGGG TGGCGAGGCTCTGGAACTC CAGGGCGTGGTGTTCAACT ACCGTACCAAGTACCCCGA CGGCACCATCTTCCCCAAGA ACGCTACTGTGCAGTCCCAA GTGATGAACACCGAGCACA AGGCTTACCTGGACAAGAAC AAGGCCTACCCCGTGGAGT GCTGGGTGCCCGACCCCAC CCGTAACGAGAACACCCGTT ACTTCGGCACCCTGACCGG TGGAGAGAACGTGCCCCCC GTGCTGCACATCACCAACAC CGCTACCACCGTGCTGCTG GACGAGTTCGGTGTCGGTC CCCTGTGCAAGGGCGACAA CCTGTACCTGTCCGCTGTG GACGTGTGCGGCATGTTCA CCAACCGTTCCGGTTCCCA GCAGTGGCGTGGCCTGTCC CGCTACTTCAAGGTGCAGCT GCGCAAGCGTCGTGTGAAG AACCCCTACCCTATCTCCTT CCTGCTGACCGACCTGATCA ACCGTCGTACCCCTCGTGT GGACGGCCAGCCCATGTAC GGCATGGACGCTCAGGTGG AAGAGGTCCGCGTGTTCGA GGGCACCGAGGAATTGCCC GGCGACCCCGACATGATGC GTTACGTGGACAAGTACGG CCAGCTCCAGACCAAGATG CTGTAA | derived from JCV | 2 |
| Protein | MAPTKRKGERKDPVQVPKLLI RGGVEVLEVKTGVDSITEVEC FLTPEMGDPDEHLRGFSKSIS ISDTFESDSPSKDMLPCYSVA RIPLPNLNEDLTCGNILMWEA VTLKTEVIGVTSLMNVHSNGQ AAHDNGAGKPVQGTSFHFFS VGGEALELQGVVFNYRTKYP DGTIFPKNATVQSQVMNTEH | wildtype JCV (AFH57194.1) | 3 |

TABLE 2-continued

Amino acid and nucleotide sequences of the VP1 protein.

| Protein/DNA | Sequence | Source | SEQ ID NO: |
|---|---|---|---|
| | KAYLDKNKAYPVECWVPDPT<br>RNENTRYFGTLTGGENVPPV<br>LHITNTATTVLLDEFGVGPLCK<br>GDNLYLSAVDVCGMFTNRSG<br>SQQWRGLSRYFKVQLRKRR<br>VKNPYPISFLLTDLINRRTPRV<br>DGQPMYGMDAQVEEVRVFE<br>GTEELPGDPDMMRYVDRYG<br>QLQTKML | | |
| DNA | ATGGCCCCAACAAAAAGAAA<br>AGGAGAAAGGAAGGACCCC<br>GTGCAAGTTCCAAAACTTCT<br>TATAAGAGGAGGAGTAGAA<br>GTTCTAGAAGTTAAAACTGG<br>GGTTGACTCAATTACAGAGG<br>TAGAATGCTTTTTAACTCCA<br>GAAATGGGTGACCCAGATG<br>AGCATCTTAGGGGTTTTAGT<br>AAGTCAATATCTATATCAGAT<br>ACATTTGAAAGTGACTCCCC<br>AAATAGGGACATGCTTCCTT<br>GTTACAGTGTGGCCAGAATT<br>CCACTACCCAATCTAAATGA<br>GGATCTAACCTGTGGAAATA<br>TACTCATGTGGGAGGCTGT<br>GACCTTAAAAACTGAGGTTA<br>TAGGGGTGACAAGTTTGATG<br>AATGTGCACTCTAATGGGCA<br>AGCAACTCATGACAATGGTG<br>CAGGGAAGCCAGTGCAGGG<br>CACCAGCTTTCATTTTTTC<br>TGTTGGGGGGAGGCTTTA<br>GAATTACAGGGGTGCTTTT<br>TAATTACAGAACAAAGTACC<br>CAGATGGAACAATTTTTCCA<br>AAGAATGCCACAGTGCAATC<br>TCAAGTCATGAACACAGAGC<br>ACAAGGCGTACCTAGATAAG<br>AACAAAGCATATCCTGTTGA<br>ATGTTGGGTTCCTGATCCCA<br>CCAGAAATGAAAACACAAGA<br>TATTTTGGGACACTAACAGG<br>AGGAGAAAATGTTCCTCCAG<br>TTCTTCATATAACAAACACTG<br>CCACAACAGTGTTGCTTGAT<br>GAATTTGGTGTTGGGCCACT<br>TTGCAAAGGTGACAACTTAT<br>ACTTGTCAGCTGTTGATGTC<br>TGTGGCATGTTTACAAACAG<br>GTCTGGTTCCCAGCAGTGG<br>AGAGGACTCTCCAGATATTT<br>TAAGGTGCAGCTAAGGAAAA<br>GGAGGGTTAAAAACCCCTAC<br>CCAATTTCTTTCCTTCTTACT<br>GATTTAATTAACAGAAGGAC<br>TCCTAGAGTTGATGGGCAG<br>CCTATGTATGGCATGGATGC<br>TCAAGTAGAGGAGGTTAGA<br>GTTTTTGAGGGAACAGAGGA<br>GCTTCCAGGGGACCCAGAC<br>ATGATGAGATACGTTGACAA<br>ATATGGACAGTTGCAGACAA<br>AAATGCTGTAA | wildtype JCV<br>(J02226) | 4 |

In a preferred embodiment of the invention, the VP1 has an amino acid sequence which is at least 90% identical to the amino acid sequence according to SEQ ID NO: 1 over its entire length.

In a preferred embodiment of the invention, the nucleotide sequence of the VP1 protein is at least 80% identical to the nucleotide sequence of SEQ ID NO: 2 over its entire length.

The structural proteins of JCV, preferably VP1, can be expressed in, for example, E. coli or in insect cells. According to a preferred embodiment of the invention, the structural proteins, preferably VP1, are expressed in insect cells. This is advantageous because the expression in insect cells leads to fewer modifications, such as post-translational modifications, compared with the wildtype protein from JCV than the expression in E. coli.

The VLP according to the invention can furthermore comprise in the capsid one or several additional heterologous proteins, i.e. proteins which are not identical to or derived from a JCV protein. For example, a heterologous protein can be anchored in the capsid, i.e. at least part of this protein being preferably accessible from the outside. In principle any protein is suitable as such a heterologous protein as long as the heterologous protein can be incorporated into the capsid and does not interfere substantially with the assembly of the VLP.

The VLP used in the drug delivery system according to invention is associated with a cargo. This means that the cargo is reversibly bound to the VLP. This can e.g. either be due to a physicochemical interaction with or attachment to any part of the capsid or by incorporation of the cargo into the capsid. The incorporation can be complete or incomplete. In a particular preferred embodiment of the invention the major part of the total amount of the cargo is fully incorporated into the capsid. Most preferred is that the cargo is fully encapsulated in the capsid of the VLP.

In the context of the invention, the expression that the "VLP comprises the cargo" is used synonymously with the expression that the VLP is "associated with the cargo". The association of the VLP and the cargo can be the result of "loading" or "packing" the VLP with the cargo.

"Loading" means any process which leads to the association of VLP and cargo, e.g. by osmotic shock or by assembly of VP1 or VP1 pentamers into VLP together with the cargo. "Loaded VLP" are the VLP resulting from this process. The term "packing" relates to the process of loading the VLP via assembly of VP1 or VP1 pentamers into VLP together with the cargo. The VLP resulting therefrom are termed "packed" VLP.

The term "cargo" is used, in the context of the present invention, for any pharmaceutical product which is associated with the VLP. The term pharmaceutical product is used in the context of the present invention interchangeably with the term "drug".

The pharmaceutical product is a therapeutic or diagnostic substance. In can be of any chemical nature as long as it associates with the VLP. Preferably the pharmaceutical product is an active pharmaceutical ingredient (API), in particular a "small molecule" (preferably an organic compound of 1000 Daltons), a biological or a cytostatics. In a preferred embodiment the biological is selected form the group consisting of a protein, a peptide or a nucleic acid, in particular selected from the group consisting of nucleic acids encoding a desired protein such as mRNA, cDNA, a plasmid or vector, inhibitory nucleic acids such as siRNA or miRNA and nucleic acids having catalytic activity such as a ribozyme.

In a further embodiment, the VLP according to the invention is loaded with a cargo which is selected from the group consisting of monoclonal antibodies, antipsychotic drugs, analgesic drugs, thrombolytics, antidepressants, immunemodulators, immunosuppressants, acetylcholinesterase inhibitors, glutamate receptor antagonists or modulators, such as NMDA receptor antagonists, psychostimulants, anti-dementia drugs, anxiolytic drugs, nootropic drugs, metabolic enhancers, metabolic modulators, neuroprotective drugs, anticonsulvants, cytostatics, and cytokines.

In a particularly preferred embodiment the cargo is a nucleic acid, in particular a nucleic acid which is suitable for RNA interference (RNAi) or gene therapy, an antibody, a cytostatic or a cytokine, more preferably the cargo is a nucleic acid such as a plasmid or an antibody. In a most preferred embodiment the cargo is a nucleic acid such as a plasmid. The term "antibody" includes antibodies or fragments thereof, as well as antibody-drug conjugates (ADC)

Preferably, the cargo is a plasmid.

In one embodiment, the nucleic acid, preferably the plasmid, comprises a gene. In case the cargo comprises a gene, its expression in the CNS target cell preferably is transient. Hence, according to a most preferred embodiment of the invention the drug delivery system comprising a VLP associated with a plasmid comprising a gene, whereas the treatment of the CNS disease is effected by the transient expression of said gene in the target cell of the subject to be treated.

According to the invention the expression "exposing" something (e.g. the VP1, pentamers, the VLP) to conditions for affecting something (e.g. inducing the assembly) refers to bringing the material under consideration (e.g. the VP1, the pentamers, the VLP) to conditions which can cause this certain effect (e.g. inducing the assembly). Such exposure may be performed by changing the conditions for the material, e.g. by bringing the material into contact with a different buffer, salt or pH etc. This is possible either by adding something to the composition comprising the material or vice versa or by separating the material from the composition and then adding the material to a different composition.

A change of conditions can also be achieved by varying temperature, radiation etc. Naturally, such means for a change of conditions can be combined and/or repeated. Other suitable conditions that induce the desired effect, such as the assembly of the VP1 or pentamers to VLP and/or inducing aggregation of the VLP, are also well known to the skilled person. The same applies to a suitable duration of the exposure to the respective conditions; this can be found out by ordinary means of the skilled person.

The expression "exposing something to conditions for affecting something" does not require the effect to be completed, i. e. not all of the material has to accomplish the effect under consideration. For example, "conditions inducing the pentamers to aggregate" essentially means that the conditions are suitable to induce aggregation. It does not require that indeed all pentamers aggregate.

As used herein, the term "assembly" or "assemble into VLP" means that the structures under consideration (either the VP1 proteins or the pentamers) associate and establish the capsid of the VLP. If the VP1 are used as the starting material the assembly into VLP may include the prior formation of pentamers, meaning that the VP1 proteins may first form pentamers and then form VLP or they may directly assemble into a VLP. The assembly to VLP is reversible.

The term "disassembly", in turn, refers to a process, when the capsid of the VLP at least partially disintegrates into pentameric structures and/or the structural proteins. The disassembly may be induced by increasing the temperature, by adding proteases and/or by decreasing intermolecular interactions used to form the VLP such as intermolecular disulfide bridges (e. g. by adding reducing agents or adding chelating agents). Such conditions may also include stepwise exposure to a condition. For instance, the composition may be contacted with a reducing agent before the temperature is increased.

Methods of inducing the VP1 and/or pentamers to assemble into VLP are generally known to the skilled person (Goldmann et al. (J. Virol. 1999; 73(5): 4465-69); DE 195 453 A1). The same applies to the disassembly of VLP into pentamers. The skilled person, hence, is aware of methods for the control of the assembly and disassembly of VLP.

In one embodiment of the invention the concentration of $Ca^{2+}$ ions in the composition containing the VP1 or pentamers is used for the control of the assembly/disassembly of the VLP. For example, in order to induce the assembly, the concentration of free $Ca^{2+}$ ions can be increased. If the disassembly is desired, the concentration of free $Ca^{2+}$ ions can be lowered by adding a chelating agent to the composition.

A further option for inducing the assembly is to increase the concentration of VP1 pentamers in order to facilitate the assembly into VLP, for example by reducing the solvent in the composition comprising the pentamers. This might require an adaption of the concentration of alkaline earth metals, such as $Ca^{2+}$ or $Mg^{2+}$.

Accordingly to a preferred embodiment of the invention, disassembly can be induced be exposing the VLP to conditions under which intermolecular disulfide bridges are reduced, for example by exposing the VLP to reducing conditions. In a preferred embodiment this step is accomplished in the additional presence of a chelating agent. More preferred, the disassembly is induced by exposing the VLP to reducing conditions in the presence of a chelating agent and optionally at an increased temperature.

In a particular embodiment of the invention, the VLP are exposed to a composition comprising DTT and EDTA and/or EGTA, preferably at a temperature of 15° C. to 30° C., preferably 20° C. to 25° C., most preferably at a temperature of about 23° C.

According to a preferred embodiment of the invention, the pentamers of the composition of c) are exposed to conditions inducing the aggregation thereof. This step is most suitable if performed before step d). In a preferred embodiment, at least 20% of the material (e. g. the pentamers) aggregates, preferably at least 30%, more preferably at least 40%.

It has surprisingly been found that this step can lead to a more homogeneous size distribution of the VLP (FIG. 7 and FIG. 8). This allows for a better quality management and standardization, which is of utmost importance if the VLP are used in a drug delivery system. Accordingly, this additional procedure preferably is part of the quality control requirements of a drug delivery system.

The term "aggregate" means any particulate structure. "Aggregation" means a process leading to aggregates. This process is reversible.

The aggregation of the pentamers or VLP can be determined by an increased average particle size of the VLP in the composition compared to the control. The larger particle size may be determined by standard methods, such as dynamic light scattering (DLS).

According to a particular embodiment of the invention, the aggregation of the pentamers or VP1 can be induced by one or more agents which are known in the art to facilitate precipitation of proteins (precipitation agent). Most preferred, according to the invention, thus is the use of a precipitation agent.

A "precipitation agent" refers to an agent that promotes aggregation of VP1 or pentamers. The concept of precipitation agents generally is known to the person skilled on the art. Precipitation agents are typically used to facilitate the concentration and purification of proteins. Precipitation can be the result of altering the solvation potential of the solvent, more specifically, by lowering the solubility of the protein. The solubility may also be decreased by adjusting the pH of the composition to the isoelectric point of a protein. Furthermore, lowering the temperature of the composition can also decrease the solubility of a protein.

Possible precipitation agents are e.g. polyethylene glycol (PEG), or alcohol, for example ethanol, and salts. The later are known to the skilled person as "agents for salting out".

Preferably, according to the invention, the precipitation agent is a salt. Most preferred are salts comprising ions known as the "Hofmeister series". The Hofmeister series describes the ordering of ions with respect to their hydrophobic effect on a specific protein in terms of their ability to affect the solubility of said protein in solution. Ions exerting a hydrophobic effect on a protein are especially preferred. Herein, such ions are referred to as kosmotropic ions.

A precipitation agent comprising at least one kosmotropic anion or cation is preferred. Preferred anions are selected from the group consisting of citrate ($C_6H_5O_7^{3-}$), phosphate ($PO_4^{3-}$), sulfate ($SO_4^{2-}$), hydrogen phosphate ($HPO_4^{2-}$), dihydrogen phosphate ($H_2PO_4$—), iodate ($IO_3^-$), hydroxide ($OH^-$), fluoride ($F^-$), bromate ($BrO_3^-$) or acetate ($CH_3COO^-$) or combinations thereof, the more preferred anions are citrate, phosphate or sulfate, the most preferred anion is sulfate.

Preferred cations are ammonium or quaternary ammonium compounds ($NR_4^+$ with R being an alkyl or an aryl group), such as tetramethylammonium ($(CH_3)_4N^+$) or dimethylammonium ($(CH_3)_2N_2^+$). Further preferred cations are selected from the list comprising potassium ($K^+$), caesium ($Cs^+$), rubidium ($Rb^+$) or lithium ($Li^+$) or combinations thereof, particularly preferred are quaternary ammonium compound or ammonium, most preferred is ammonium.

Therefore, the salt preferably comprises an anion and a cation selected from the group consisting of citrate ($C_6H_5O_7^{3-}$), phosphate ($PO_4^{3-}$), sulfate ($SO_4^{2-}$), hydrogen phosphate ($HPO_4^{2-}$), dihydrogen phosphate ($H_2PO_4$–), iodate ($IO_3^-$), hydroxide ($OH^-$), fluoride ($F^-$), bromate ($BrO_3^-$) or acetate ($CH_3COO^-$), quaternary ammonium compounds ($NR_4^+$) with R being an alkyl or an aryl group, preferably tetramethylammonium ($(CH_3)_4N^+$) or dimethylammonium ($(CH_3)_2N_2^+$), ammonium ($NH_4^+$), potassium ($K^+$), caesium ($Cs^+$), rubidium ($Rb^+$) or lithium ($Li^+$), preferably comprising $So_4^{2-}$ and/or $NH_4^+$ or combinations thereof.

According to a preferred embodiment the salt is selected from the group consisting of $(NH_4)_2SO_4$, $K_2SO_4$, $Na_2SO_4$, $(NH_4)_2HPO_4$, $K_2HPO_4$ and $Na_2HPO_4$ The most preferred salt is ammonium sulfate ($(NH_4)_2SO_4$).

According to the invention, the aggregation of the pentamers can be induced by any means for bringing the pentamers into contact with the precipitation agent, for example by adding the precipitation agent to the composition comprising the pentamers or vice versa, namely adding the composition comprising the pentamers to a precipitation agent. Also other means, such as a dialysis so that the precipitation agent reaches the pentamers by diffusion, is possible.

According to one preferred embodiment of the present invention, the aggregation of the pentamers is induced by a dialysis against a composition comprising the precipitation agent, for example a composition comprising ammonium sulfate.

According to a particularly preferred embodiment of the invention, the composition containing the pentamers for aggregation, has an ammonium sulfate concentration between 0.3 to 5 M, preferably up to 4 M, even more preferred is a concentration between 1.8 and 2.2 M. Most preferred is around 2 M.

The step of inducing aggregation of the pentamers preferably has a duration of at least 1 hour, more preferred of at least 5 hours, even more preferred of at least 12 hours, most preferred of at least 16 hours. It is preferred that the step has a duration is less than 24 hours. In a preferred embodiment the duration of this step is between 14 and 19 hours. In a most preferred embodiment the duration of this step is between 16 and 18 hours. During this time the pentamers are in exposed to conditions for inducing aggregation, in particular they are in contact with ammonium sulfate.

After the step of inducing the aggregation of the pentamers, it is advantageous to include into the process of the invention a step of separating the pentamers from the conditions which had been uses for inducing the aggregation. The methods applicable for such a step are not particularly limited; any method known to the skilled person, which allows for the separation of the pentamers from the aggregation inducing conditions is applicable.

In a preferred embodiment of the invention the pentamers are separated from the conditions inducing their aggregation by dialysis. Dialysis can be used if the aggregation of the pentamers is induced by using a precipitation agent. The principle of dialysis can also favorably be applied in order to bring the pentamers into contact with a precipitation agent. Most preferred is, if the method according to the invention includes at least two steps of dialysis: a first dialysis of the composition of step c) against a composition comprising a precipitation agent, and a second dialysis after the induction of aggregation against a composition which is essentially free of the precipitation agent.

The dialysis for separating the pentamers from the precipitation agent preferably is against a composition which is at least similar to physiological conditions. Such a composition preferably comprises a salt and has a pH of 6 to 8.5, preferably of 6.5 to 8.5, more preferably of 7 to 8, most preferably of 7.2 to 7.5, in particular 7.5. The osmolarity of the composition is preferably between 280 and 310 mosmol/l, most preferably 308 mosmol/l. The composition may for example have a saline (sodium chloride) concentration of 0.8 to 0.92% (w/v), preferably of 0.9% (w/v).

Separating the pentamers from the conditions which had been used for inducing the aggregation is preferably performed for at least 1 hour, more preferred for at least 5 hours, 12 hours, more preferably for at least 18 hours, more preferably for about 24 hours or longer. Longer time periods are also possible inter alia depending on the concentration of the pentamers which had been induced to aggregate, the composition comprising the pentamers and the nature and concentration of the precipitation agent. In a preferred embodiment, the composition comprising the aggregated pentamers is dialyzed against a composition similar to physiological conditions for about 24 hours.

The composition preferably further contains a buffer. Suitable buffering systems are known to the skilled person. In a preferred embodiment of the invention the composition includes a TRIS buffer, HEPES buffer, a phosphate buffer or a bicarbonate buffer system. Most preferred is a TRIS buffer.

In a most preferred embodiment the composition comprises 10 mM Tris-HCl and 150 mM NaCl and has a pH of 7.5.

In order to facilitate assembly of the pentamers into VLP, the composition may further comprise divalent ions, such as $Ca^{2+}$, $Mg^{2+}$, $Ba^{2+}$, $Cu^{2+}$, $Fe^{2+}$, $Zn^{2+}$ or combinations thereof. Most preferred is $Ca^{2+}$, for example $CaCl_2$. In a preferred embodiment, the composition comprises 1 to 3 mM $CaCl_2$, preferably 2 mM $CaCl_2$.

In a very preferred embodiment of the invention, the composition which is at least similar to physiological conditions comprises 10 mM Tris-HCl, 150 mM NaCl and 2 mM $CaCl_2$ and has a pH of 7.5.

Figure 5:
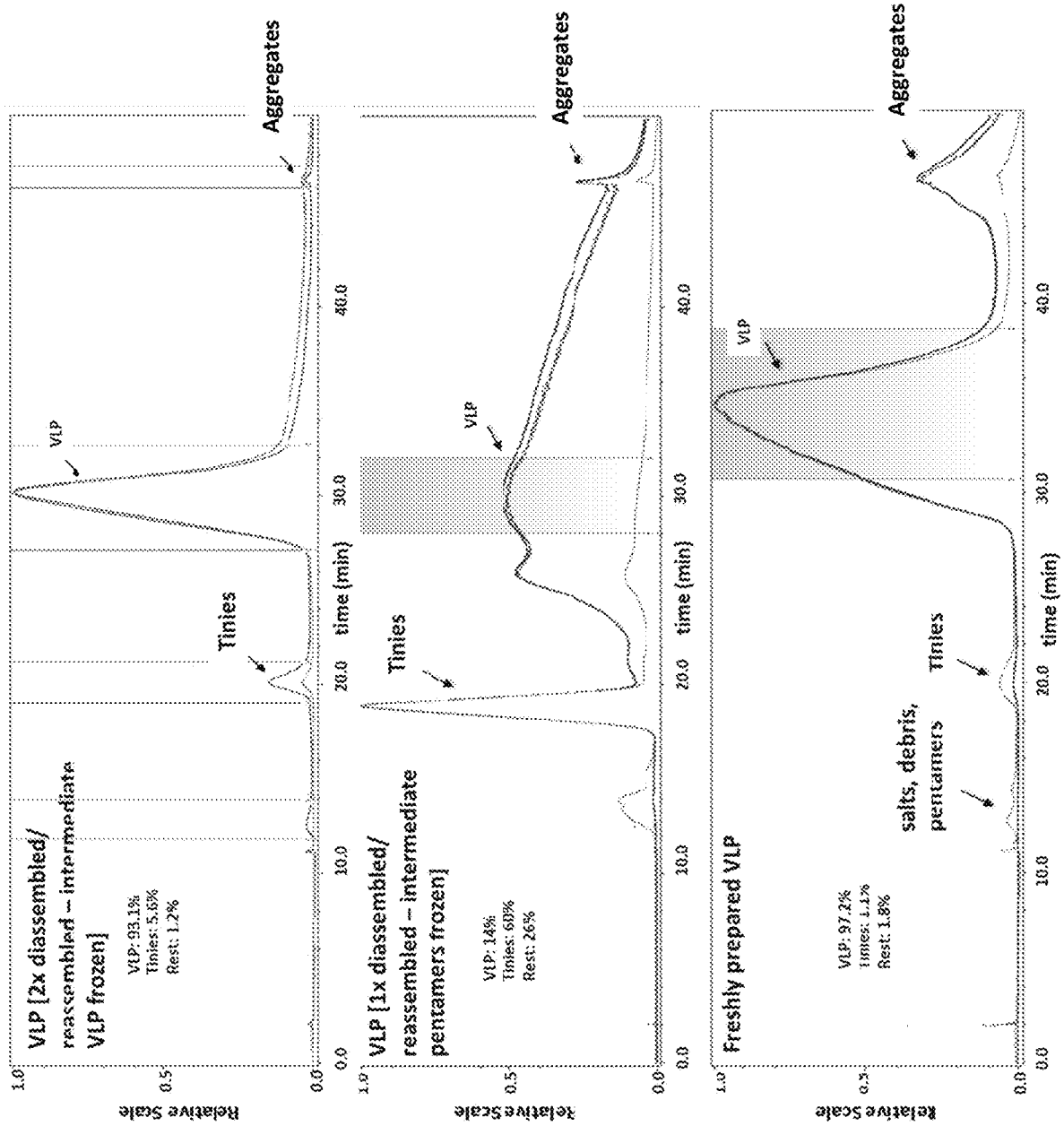

In yet another aspect of the invention it has surprisingly been found that the storage of VLP (rVLP) is advantageous compared with the storage of pentamers (FIG. 4 and FIG. 5). If pentamers are stored and subsequently thawed and reassembled, predominantly "tiny" particles form as well as aggregates. These VLP are not suitable for the production of a drug delivery system. VLP, however, that have been dissociated and reassembled after storage form a particularly homogeneous population of adequately sized VLP. Thus, in one embodiment of the invention a composition is provided with particles having an average diameter from 20 nm to 70 nm, preferably of 30 nm to 70 nm, more preferably of 35 nm to 65 nm, more preferably of 40 to 60 nm. A homogeneous size distribution is important in order to fulfill quality control requirements.

In a preferred embodiment, the method according to the invention comprises a step of storing the VLP from the composition of step d). Storing the VLP at a temperature of about −80° C. to about 4° C. at is possible for a duration of at least 10 h, 15 h, 20 h, preferably for at least 24 h. A storage of even more than 3 days is possible.

In a preferred embodiment the VLP are stored at a temperature below 0° C. (freezing). Freezing may be performed using different cooling rates. For example "slow" freezing may occur by applying a cooling rate of about −1° C. per minute, while fast freezing may be performed by contacting the sample, i. e. the container which comprises the composition, with liquid nitrogen or by placing the sample in a freezer at −80° C.

In a preferred embodiment, storing takes place in a composition comprising a cryoadditive, preferably selected from the group comprising polyols, sugars, inorganic salts, organic salts, amino acids, polymers, extremolytes or derivatives or combinations thereof.

In a preferred embodiment, the inorganic salt comprises a sulfate anion. Preferred salts comprising a sulfate anion are potassium sulfate, sodium sulfate, sodium thiosulfate, magnesium sulfate and ammonium sulfate. Preferably, the inorganic salt is ammonium sulfate.

The amino acid preferably is glycine, glutamine, proline or alanine. A preferred amino acid derivative is betain. Further possible cryoadditives are glycerol, sucrose, DMSO, ectoin or hydroxyectoin.

It has been found that the addition of cryoadditives, in particular the addition of an inorganic salt (such as a salt comprising a sulfate anion, in particular ammonium sulfate) and/or an amino acid derivative (such as betain), is advantageous with respect to the stability and the functionality or efficacy of the VLP (FIG. 9). As stated supra, an enhanced stability and/or functionality or efficacy is particularly desired when using VLP as a drug delivery system. It was surprising that the addition of cryoadditives to the composition of step d) has an impact on the packed VLP of step f) in terms of stability and functionality or efficacy.

A cryoadditives serves the purpose of protecting biological tissue from freezing damage (i.e. due to ice formation). The cryoadditives usually operate by increasing the solute concentration in cells. However, in order to be suitable for biological use they must easily penetrate and must not be toxic to cells. Such additives are thus suitable to provide milder storing conditions for the pentamers and/or VLP. Cryoadditives can be supplemented to a composition comprising pentamers and/or VLP to be frozen for storage.

According to a particular preferred embodiment of the present invention, the cryoadditive is added to the composition comprising VLP for subsequent freezing after the VLP, preferably rVLP, were assembled using two dialysis steps (two-step reassembly).

Suitable molar concentrations of cryoadditives except for the polyol-based cryoadditives may be 0.5 M, 0.6 M, 0.7 M, 0.8 M, 0.9 M, 1 M, 1.1 M, 1.2, 1.3 M, 1.4 M, 1.5 M, 2 M, 3 M, 4 M, 5 M. Preferentially, these cryoadditives are used at a molar concentration of about 1 M, preferably at a molar concentration of 1 M.

The polyol-based cryoadditive may be used at molar concentrations of at least 0.3 M, at least 0.4 M, at least 0.5 M, at least 0.6 M, at least 0.7 M, at least 0.8 M, at least 0.9 M, at least 1 M, at least 2 M or at least 3 M. Preferably, the polyol-based cryoadditives, preferably glycerol 5%, may be used at a concentration of about 0.6 M to 0.7 M, more preferably at a concentration of 0.68 M.

Alternatively, the polyol-based cryoadditive may be added based on volume percent of the composition comprising pentamers and/or VLP. Suitable volume percent include 3% (v/v), 4% (v/v), 5% (v/v), 6% (v/v), 7% (v/v), 8% (v/v), 9% (v/v) or 10% (v/v). Preferentially, the polyol-based cryoadditive is added at 5% (v/v).

In a preferred embodiment of the invention, the pentamers of step c) and/or the VLP of step d) are subject to purification. The term "purification" in the context of the present invention refers to isolating or separating the VP1, pentamers or VLP from a complex composition. Possible methods include precipitation, cross flow filtration, chromatography, for example a preparative chromatography, preferably size exclusion chromatography, and/or dynamic light scattering (DLS).

The term "chromatography" refers to a method which permits the separation of a mixture of substances by distributing the individual components thereof between a stationary phase and a mobile phase. In particular, chromatography refers to a method of purifying a substance by first binding and enriching the substance of interest to the stationary phase before eluting it in a second step (bind-and-elute mode of chromatography) or by binding impurities to the stationary phase and increasing the purity of the molecule of interest in the flow-through (flow-through mode).

Chromatography can be grouped according to the basis of the interaction of the analyte comprised in the mobile phase with the stationary phase. Preferred types of chromatography according to the invention encompass "reversed phase" chromatography, "ion-exchange" chromatography, "affinity" chromatography, or size exclusion chromatography (SEC). Among ion-exchange chromatography, the purification method can be further separated based on the charge present in the stationary phase into cation-exchange chromatography (CEX), in which the stationary phase has a negative charge, thus retaining positively charged molecules, and anion exchange chromatography (AEX), in which the stationary phase has a positive charge, thus retaining negatively charged molecules.

In particular, chromatography may be used to purify rVLP obtained by the method according to the present invention as an intermediate product. In particular AEX may be used to purify rVLP.

The stationary phase used in AEX can be further described based on the strength of the ionic interaction provided by the exchanging material present in the stationary phase into "strong anion exchangers" and "weak anion exchangers". The expressions "anion exchanger" or "anion exchange matrix" are synonymous and both refer to natural or artificial substances which can bind anions and can exchange these for anions from a surrounding medium. An anion exchanger carries positive ions and exchanges negatively charged counterions.

The VLP of the invention may be further treated with a nuclease and/or be subjected to sterile filtration. A nuclease treatment is preferably done if a nucleic acid is used as cargo. Different nucleases are known to the skilled person and include for example benzonase. Methods for sterile filtration include, inter alia diafiltration or ultracentrifugation using filters suitable for the removal of impurities.

In yet another aspect of the invention, a composition comprising virus-like particles (VLP) derived from John Cunningham virus (JCV) is provided, which is characterized by one or more of the following parameters:

a. a polydispersity index (PDI) of less than 0.3, preferably less than 0.2, preferably less than 0.1, more preferably in a range between 0.01 and 0.09,
b. at least 70% of VLP with an average diameter from 20 nm to 70 nm, preferably of 30 nm to 70 nm, more preferably of 35 nm to 65 nm, more preferably of 40 to 60 nm,
c. a VLP content within the composition of at least 80% (v/v), preferably at least 85% (v/v), preferably at least 90% (v/v), preferably at least 95% (v/v).

The particle size distribution can be assessed as the "Poly Dispersity Index" (PDI). The PDI indicates the distribution of particle sizes in a composition, and thus describes the uniformity of particles. PDI values can be obtained using different methods, including gel permeation chromatography/size exclusion chromatography, rheology, solution viscosity, membrane osmosis or light scattering.

The PDI preferably is determined by dynamic light scattering (DLS). In DLS, the native distribution is the intensity distribution which indicates how much light is scattered from the various "slices". DLS allows determination of the mean size and the standard deviation from this mean size from the statistics of the distribution. Relative polydispersity can be determined by dividing the standard deviation by the mean. From the relative polydispersity of a distribution the polydispersity index (PDI) can be derived as its square. PDI values obtained by DLS can be grouped into monodispersed (PDI<0.1) compositions and polydispersed (PDI>0.1) compositions, whereby also within the polydispersed group smaller values indicate a more uniform distribution within the composition.

According to the invention, PDI values of 0.1 to 0.4 are preferred. More preferably, the PDI value is 0.1 to 0.3 and even more preferably 0.1 to 0.2.

The average diameter of a composition comprising VLP may be measured by visual methods, such as microscopy, preferably equipped with software to determine the average diameter, but also by analytic light scattering methods, such as DLS or nanotracking method, such as NTA.

The VLP content within the composition can be measured by, for example, FFF-MALS and/or DLS. Both methods can distinguish between the right-sized VLP and aggregates, "tinies" (small particles) and other impurities, such as salts, debris or pentamers.

Such a composition in particular fulfills requirements usually imposed on a drug delivery system. Obviously, such a composition is homogeneous and has a high purity.

In another aspect, the invention relates to a drug delivery system obtainable by the method according to the invention. Such a drug delivery system has the advantages as stated supra. In particular, such a drug delivery system can be used in a method of therapy and/or diagnosis, preferably for the treatment of neurological disorders, i. e. CNS diseases.

Hence the invention also relates to a method of treating a disorder, in particular a CNS disease, with the drug delivery system according to the invention. The method of treating preferably comprises the step of administering the drug delivery to a subject in need thereof.

The invention also relates to the use of the drug delivery system for the manufacture of a medicament for the treatment of neurological disorders, i. e. CNS diseases. The method of treatment preferably does not comprise a step of increasing the permeability of the BBB of the subject to be treated. The drug delivery system of the invention, preferably, is administered to a patient who has not received any chemical or physical treatment for impairing or disrupting the BBB.

The term "CNS diseases" (or "neurological disorders") refers to any disorder of an individual's nervous system, preferably of the central nervous system. It encompasses neurodegenerative, psychotic or neurovascular disorders.

In one embodiment of the invention, the neurological disorder is selected from the group consisting of stroke, alcohol addiction, Alzheimer Disease, anxiety, arthritis, asthenia, attention deficit hyperactivity disorder, bipolar disorder, cancer pain, cerebral ischemia, cerebral neuroprotectant, cervical dystonia, Chorea associated with Huntington's disease, chronic pain, chronic severe pain, cognitive disorder, cortical myoclonus, degenerative Nerve Diseases, depression, diabetic neuropathic pain, diabetic neuropathy, emotional lability, epilepsy, excessive sleepiness associated with narcolepsy, fibromyalgia, Fragile X syndrome, Friedreich's ataxia, insomnia, Lennox Gastaut syndrome, major depressive and anxiety disorders, manic episodes associated with bipolar disorder, memory impairment, migraine, mild cognitive impairment, moderate to severe pain, motor neuron disease, multiple sclerosis, musculoskeletal pain, narcolepsy, neuralgia, neuropathic pain, nicotine dependence, obsessive compulsive disorder, opioid-induced adverse effect, opioid-induced constipation, osteoarthritis pain, overactive bladder, pain, Parkinson's disease, pediatric drooling, peripheral diabetic neuropathy, post-operative pain, postherpetic neuralgia, premenstrual dysphoric disorder, psychosis, refractory complex partial seizures, restless leg syndrome (RLS), schizophrenia, seizure, severe chronic pain, sleep disorder, smoking cessation, spasticity, spinal cord injury, stroke, transthyretin familial amyloid polyneuropathy, traumatic brain injury, vertigo, cachexia, amyotrophic lateral sclerosis, spinocerebellar ataxia type I, extrapyramidal and movement disorders, transient ischemic attack (TIA), Progressive multifocal leukoencephalopathy (PML), HIV-infection, dementia, such as Alzheimer's disease, vascular dementia, frontotemporal dementia, semantic dementia and dementia with Lewy bodies, and preferably selected from the group comprising or consisting of Alzheimer's disease, Parkinson's disease and multiple sclerosis.

In a further aspect of the invention, the invention relates to a virus-like particles (VLP) derived from John Cunningham virus (JCV) obtainable by a method comprising steps a) to e) of the inventive method and a further step of exposing the pentamers of the composition of e) to conditions inducing the pentamers to assemble into VLP. No cargo is added in the final assembly step. Such a VLP may be particularly useful as a vaccine.

In one embodiment, the VLP according to the invention cross the blood brain barrier (BBB). Therefore, in one embodiment of the invention, the drug delivery system may be used to deliver a drug across the BBB. According to the invention, a drug delivery system and/or a VLP and/or the drug the VLP is packed with may cross the BBB.

Importantly, the crossing of the BBB by the drug delivery system enables the drug delivery system to exhibit is function of targeting specific cell populations within the brain, i.e. deliver a cargo to targeted cells. In the context of the invention said drug delivery system comprises a delivery to and/or into the targeted cells.

In a preferred embodiment, the VLP of the invention and/or its cargo, after administration to the subject to be treated, in particular a human, can be detected in the CNS in less than 10 days, preferably in less than 5 days, more preferably in less than 3 days after administration. The drug delivery system preferably is administered to the subject intravenously. This is particularly advantageous when using the VLP as a reliable drug delivery system.

Preferably, the method does not require a loss of integrity or increased permeability of the BBB.

The integrity of the BBB in vitro may be measured by known methods, for example by relative transendothelial electrical resistance measurement (TEER) (Rempe et al., Biochem Bioph Res Comm 2011, 406 (1): 64-69). Many in vitro models of BBB are established, including primary bovine or human brain endothelial cells in different co-cultures, for example the human brain endothelial cell line HBEC-5i. In vivo, imaging methods, such as CT scans or MRI, can be used together with contrast agents to visualize BBB permeability. Functional imaging, such as PET or SPECT, may also be used.

According to the invention, it is not required to impair the permeability of the BBB prior or while administering the drug delivery system. Thus, the BBB is preferably physiologically intact which means that the integrity is not decreased and/or the permeability not increased compared with the healthy, native state. The VLP of the invention preferably cross the physiologically intact BBB.

The composition comprising the drug delivery system preferably does not require an additive that may disrupt the integrity of the BBB. Hence, in a most preferred embodiment of the invention the drug delivery system is free of any additive that can impact the permeability of the BBB.

Materials and Methods

VLP Manufacturing

Virus-like particles (VLP) were manufactured by protein expression using a Sf9 insect cell line derived from the fall armyworm (*Spodoptera frugiperda*) (Thermo Fischer scientific). VLP were produced by infecting the cells with recombinant Baculovirus containing a John Cunningham virus VP1-protein expression cassette. The recombinant Baculovirus was prepared by using the Bac-to-Bac® Baculovirus expression system (Thermo Fischer Scientific). VLP were produced at pH 6.3 after 7 to 10 days in a 3.4 L bioreactor (INFORS HT Minifors). Air flow and temperature (26° C.) were controlled over the time. To remove cells and cell debris suspension was centrifuged at 4° C., 5.000 g and the supernatant containing VLP was harvested.

After that VLP were concentrated using two different concentration methods: precipitation with 7.5% polyethylenglycol (PEG) or cross flow with an ÄKTAcross flow™ system (GE Healthcare). For PEG precipitation the clarified supernatant was mixed with PEG to achieve 7.5% (v/v) and incubated for 2 h at 4° C., after that the precipitate was separated by centrifugation at 4° C., 10.000 g and suspended in 50 mM NaCl, 10 mM Tris-HCl, pH 7.5. Cross flow was performed with an ÄKTAcross flow™ system equipped with a 300 kDa cut-off membrane (Hydrosart® 300kDa ECO, Sartorius). The flow ultrafiltration was carried out with a constant pressure of 1.5 bar and a factor of 8 (1 L supernatant against 8 L buffer).

VLP were further dissociated to pentamers by using 5mM DTT and 10 mM EDTA for 70 min at room temperature and the pentamers purified by anion exchange chromatography (AEX) using HiScale CaptoQ column (GE Healthcare) with a NaCl step gradient from 150 mM to 1M NaCl. Pentamers were eluted with a 250 mM NaCl step. After elution the pentamers were processed as follows:

a) Mixed with cargo and reassembled (see "Packaging of fresh or stored pentamers with cargo");
b) Frozen at −80° C. with 5% glycerol for storage of pentamers (which can subsequently be mixed with cargo and reassembled, see "Packaging of fresh or stored pentamers with cargo") or
c) Immediately placed into dialysis cassettes with 20 kDa cut-off (Slide-A-Lyzer™ G2 Dialysis Device, Thermo Scientific) and reassembled by two-step-reassembly by dialysis (two-step dialysis). First, pentamers were dialyzed against 2 M ammonium sulfate buffer ("AS", 10 mM Tris-HCl, 150 mM NaCl, 2 M $(NH_4)_2SO_4$, pH 7.5) for 24 h and then transferred for the next 24 h into 10 mM Tris-HCl, 150 mM NaCl, 2 mM $CaCl_2$, pH 7.5 (standard reassociation buffer, "ST") (AS>ST). Alternatively, the two-step dialysis was performed with ST buffer in both steps (ST>ST). In both cases, to separate not reassembled material and aggregates from the VLP, the composition comprising the VLP was purified by size exclusion chromatography (SEC) using HiPrep™ Sephacryl® S-500 HR column (GE Healthcare) under control of polydispersity index (PDI) of fractions in dynamic light scattering (DLS) using Zetasizer ZS Nano (Malvern Inc.). VLP fraction with targeted size were selected and pooled, and then concentrated in Vivaspin® concentrators (Sartorius) with 5 kDa cut-off membrane, if applicable followed by storage at −80° C.

Packaging of Reassembled VLP with Cargo

For VLP packaging of reassembled VLP, stored VLP of step c) above were taken from −80° C. and thawed using a thermal shaker (23° C., 350 rpm). Subsequently, dissociation of thawed VLP samples was performed by incubating the samples for 15 min at 23° C. and 45 rpm in the presence of dissociation buffer (20 mM Tris-HCl, 150 mM NaCl, 5 mM DTT, and 10 mM EDTA). Dissociated VLP were reassembled in the presence of cargo (e.g., nucleic acid). In short, the dissociated VLP were mixed thoroughly with the cargo in appropriate concentrations followed by dialyzing the mixture against standard reassociation buffer (10 mM Tris-HCl, 150 mM NaCl, 2 mM $CaCl_2$, pH7.5) using a 20 kDa MWCO dialysis chamber (Slide-A-Lyzer™ MINI Dialysis Device, Thermo Scientific). After 4 to 6 h, dialysis buffer was replaced by fresh dialysis buffer and samples were incubated for additional 16 to 18 h. In case of using nucleic acids as cargo, unpacked nucleic acids were digested by incubation with 40 u Benzonase® Nuclease (Merck) per 25 μg VLP and 2.5 mM $MgCl_2$ at 37° C. for 1 h. Samples were filtrated (Corning® Costar® Spin-X® centrifuge tube filters; pore size 0.22 μm) before analysis. VLP were directly analyzed afterwards and/or stored at −80° C.

Packaging of Fresh or Stored Pentamers with Cargo

For pentamer packaging, fresh or at −80° C. stored pentamers were directly mixed and reassembled with cargo or thawed using a thermal shaker (23° C., 350 rpm), and then reassembled in the presence of cargo (e.g., nucleic acid). In short, the pentamers were mixed thoroughly with the cargo in appropriate concentrations followed by dialyzing the mixture against standard reassociation buffer (10 mM Tris-HCl, 150 mM NaCl, 2 mM $CaCl_2$, pH7.5) using a 20 kDa MWCO dialysis chamber (Slide-A-Lyzer™ MINI Dialysis Device, Thermo Scientific). In case of using nucleic acids as cargo, unpacked nucleic acids were digested by incubation with 40 u Benzonase® Nuclease (Merck) per 25 μg reassembled VLP and 2.5 mM $MgCl_2$ at 37° C. for 1 h. Reassembled pentamers were directly analyzed afterwards.

Functionality Testing of VLP/Luciferase Assay

In case of VLP loaded with nucleic acids (manufactured from fresh or stored pentamers; or from reassembled and purified VLP) luciferase NanoLuc® plasmid has been used as cargo. Glioblastoma cells were seeded 24 h in advance with a density of $3*10^4$ in 900 μl DMEM medium, high glucose, GutaMAX™ (Thermo Fisher) supplemented with 10% FCS (Thermo Fisher) and 1% Pen-Strep (PAN-Biotech). Prior to adding the sample the corresponding amount of media was removed for keeping a constant amount of medium in each well. Samples were added to the cells and incubated for 48 h at 37° C. and 5% $CO_2$ After that cell medium was eliminated and cells were washed with PBS. Luciferase activity was determined according to the manufacturer's instructions (NanoGlo® Luciferase Assay (Promega)). Luminescence was measured in white 96-well plates (Greiner bio-one) in Glomax® Multi detection system (Promega).

VLP Characterization

For verifying sample dissociation, reassembly and stability, dynamic light scattering (DLS) and polydispersity indices (PDI) of the samples were measured using a Zetasizer Nano ZS (Malvern.). The VLP sizes and PDI were documented with Zetasizer Software (version 7.11, Malvern). Additionally, inflection temperatures for each sample were assessed by nDSF using a Tycho NT.6 (Nanotemper).

To analyze sample composition, asymmetric flow field flow fractionation (AF4, Wyatt Inc.) was performed. Samples were analyze by using multiangle light scattering (MALS), dynamic light scattering (DLS) and UV detector.

Transmission electron microscopy (TEM) analyses were carried out for directly visualizing the sample at different experimental steps with help of a Zeiss EM900 electron microscope, operating at a voltage at 80 kV. For this approach, samples were stained on carbon-coated copper grids (Plano GmbH) using 2% uranyl acetate (Sigma Aldrich) beforehand.

Artificial Blood-Brain-Barrier (BBB) Model for Verifying BBB Permeation

BBB permeation of VLP was assessed by either using monoculture (direct quantification of permeated fluorescently labeled-material) or co-culture (protein expression caused by permeated material in target cells) in a two-compartment artificial BBB model.

In both cases, 24-well permeable supports (insert, 0.4 μm, Corning Costar) were coated for 90 min at 37° C. with a mixture of 1:20 Fibronectin (BioReagent) and 1:75 Collagen Type I (Merck Millipore) in phosphate buffered-saline (PBS) in advance. After carefully removing the excess coating, coated inserts were transferred to a fresh 24-well plate (Greiner Bio-One) filled with 900 μl medium (Endo-GRO, SCME004, Merck Millipore). $7.5*10^4$ BBB cells (HBEC-5i, cerebral microvascular endothelium) were seeded into the inserts with 200 μl medium. Cells were incubated for 96 h to 120 h with exchanging the media in the wells every second day.

Monoculture Experiments (Permeation of Fluorescently Labeled Cargo)

The prepared inserts were carefully transferred to a fresh 24-well plate filled with 900 μl of phenol-free medium (DMEM/F-12, HEPES, no phenol red, Thermo Fisher Scientific) per well. Prior to adding the sample to the insert, the corresponding amount of media was removed, for keeping a constant amount of 200 µl medium in each insert. After 120 min of incubation at 37° C. in an incubator, 3×100 µl of each well were transferred to a black 96-well plate and the fluorescence of the sample was determined using a plate reader (Tecan Infinite M200, Tecan).

To confirm BBB formation, the BBB was disrupted by the addition of EDTA to the insert. The inserts were transferred to a 24-well plate containing fresh phenol-free media. EDTA ($c_{End}$=5 mM, approx. 5 µl) was added to the inserts and incubated for 90 min at 37° C. Afterwards, fluorescence was determined as described above.

Permeation was calculated by normalizing the fluorescence signal of the inserts harboring BBB cells to the appropriate inserts without BBB cells. In the same manner, the integrity of the BBB was verified after the addition of EDTA.

Co-Culture Experiments (Activity of Permeated Material)

Inserts were transferred to a fresh 24-well plate, containing target cells (glioblastoma cells), that were seeded 24 h in advance with a density of $3*10^4$ in 900 µl DMEM, high glucose, GutaMAX™ (Thermo Fisher) supplemented with 10% FCS (Thermo Fisher) and 1% Pen-Strep (PAN-Biotech). Prior to adding the sample (VLP packed with Nano-Luc® plasmid) to the insert, the corresponding amount of media was removed for keeping a constant amount of 200 µl medium in each insert. After 24 h, the insert was removed from the 24-well plate and washed using PBS. Accordingly, the membrane (harboring the BBB cells) was cut out using a scalpel and transferred to a 1.5 ml reaction vial. Luciferase activity was determined according to the manufacturer's instructions (NanoGlo® Luciferase Assay (Promega)).

The wells (containing the target cells) were incubated for another 24 h before the luciferase assay was performed according to the manufacturer's instructions (NanoGlo® Luciferase Assay (Promega)).

Storage with Cryoprotection

Each cryoadditive glycerol (Carl Roth), sucrose (Carl Roth), ammonium sulfate (Carl Roth), DMSO (Carl Roth) and betaine (Merck) was added to VLP resulting in a final additive concentration of 1 M, except for glycerol with 5% (v/v) corresponding to 0.68 M. Additionally, one aliquot did not contain an additive substance (w/o). The samples were splitted and frozen by applying two freezing speeds: One half of each sample was frozen with a cooling rate of approx. −1° C./min (slow freezing), while the second half was frozen fast by dipping the containers into liquid nitrogen (fast freezing). All samples were stored at −80° C. with a storage period of 1 to 10 days. After thawing at 23° C. and shaking at 350 rpm, the samples were dialyzed against 10 mM Tris-HCl, 150 mM NaCl, 2 mM $CaCl_2$, pH 7.5 at room temperature for 2 h to reduce additive concentration and their impact on analysis results. Particle diameter and PDI were determined by a Zetasizer Nanoseries (Malvern). Inflection temperatures were measured using a Tycho NT.6 (Nanotemper). VLP functionality after storage was proved with help of NanoLuc® plasmid packaging and subsequent NanoGlo® Luciferase assay (Promega).

EXAMPLES

Example 1: Functional Analyses

The cargo delivering efficacy of VLP, which were prepared using different methods, was compared (FIG. 1). To this end, VLP were generated that underwent two rounds of disassembly and subsequent reassembly or one round of disassembly and subsequent reassembly (in both methods, last reassembly in the presence of a luciferase plasmid). Remarkably, Luciferase activity of VLP that underwent two rounds of disassembly and subsequent reassembly was significantly increased compared to VLP that underwent one round of disassembly and subsequent reassembly and compared with the "plasmid only" and "cells only" controls.

Figure 2B:
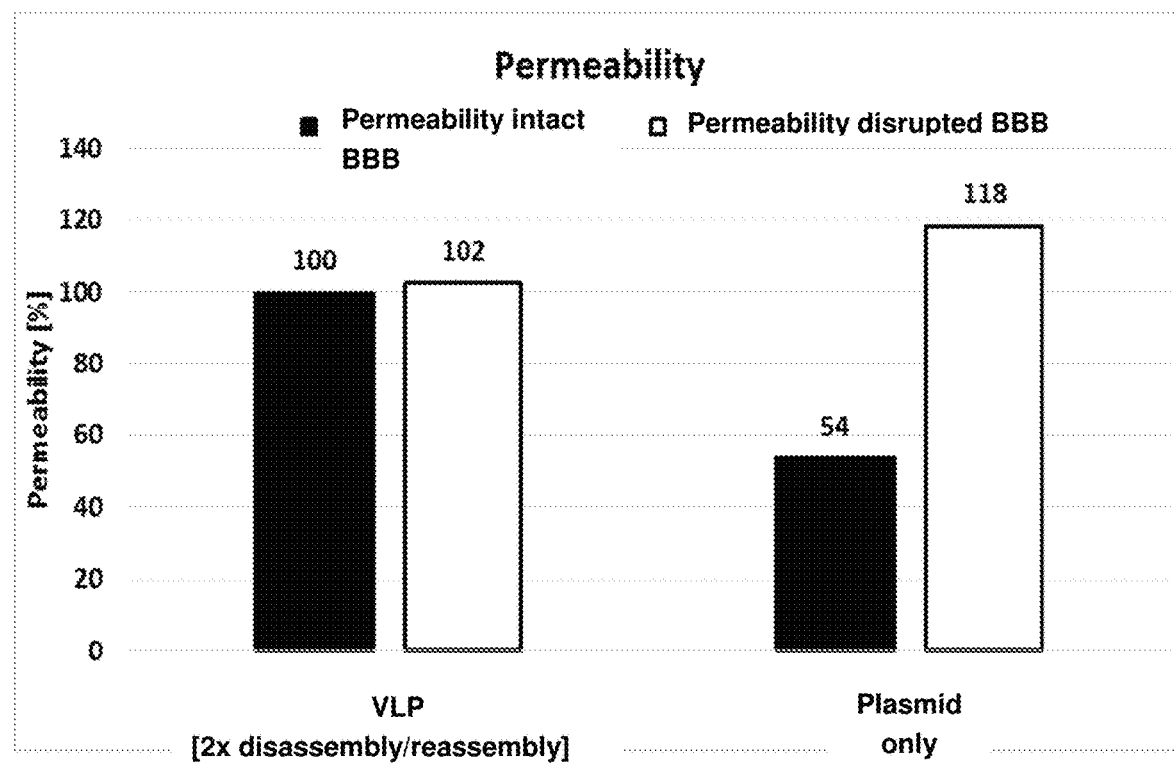

Next, the ability of VLP prepared according to the present invention to penetrate the blood-brain-barrier (BBB) was analyzed (FIG. 2). FIG. 2A shows the setup of an artificial blood-brain-barrier (BBB) model for testing BBB permeation by VLP or plasmid (circles) in a monoculture setup. Human brain endothelial cells (BBB cells, HBEC-5i) were plated on the permeable support. FIG. 2B shows the permeability of the VLP that underwent two rounds of disassembly and subsequent reassembly (second reassembly in the presence of a fluorescently labeled plasmid) compared with a "plasmid only" control. The black columns represent experiments with the intact BBB. The white columns represent experiments with an artificially disrupted BBB (by the addition of EDTA). Strikingly, VLP prepared according to the present invention were capable to cross the BBB in significantly larger ratios than naked plasmid. Disruption of the integrity of the BBB layer destroyed this difference, showing the selective, efficient penetration capacity of VLP prepared according to the present invention.

Figure 3A:
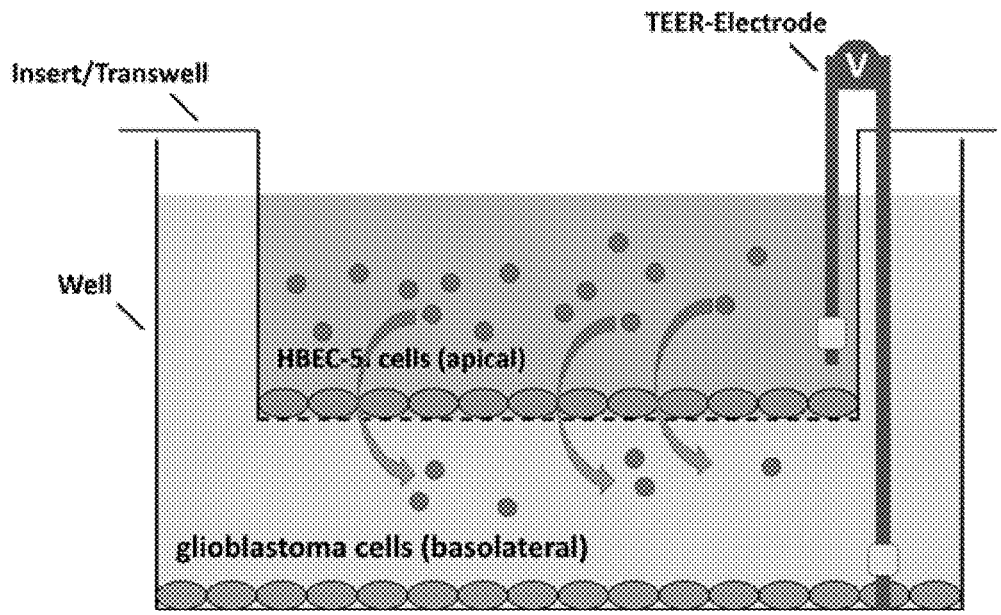
Figure 3B:
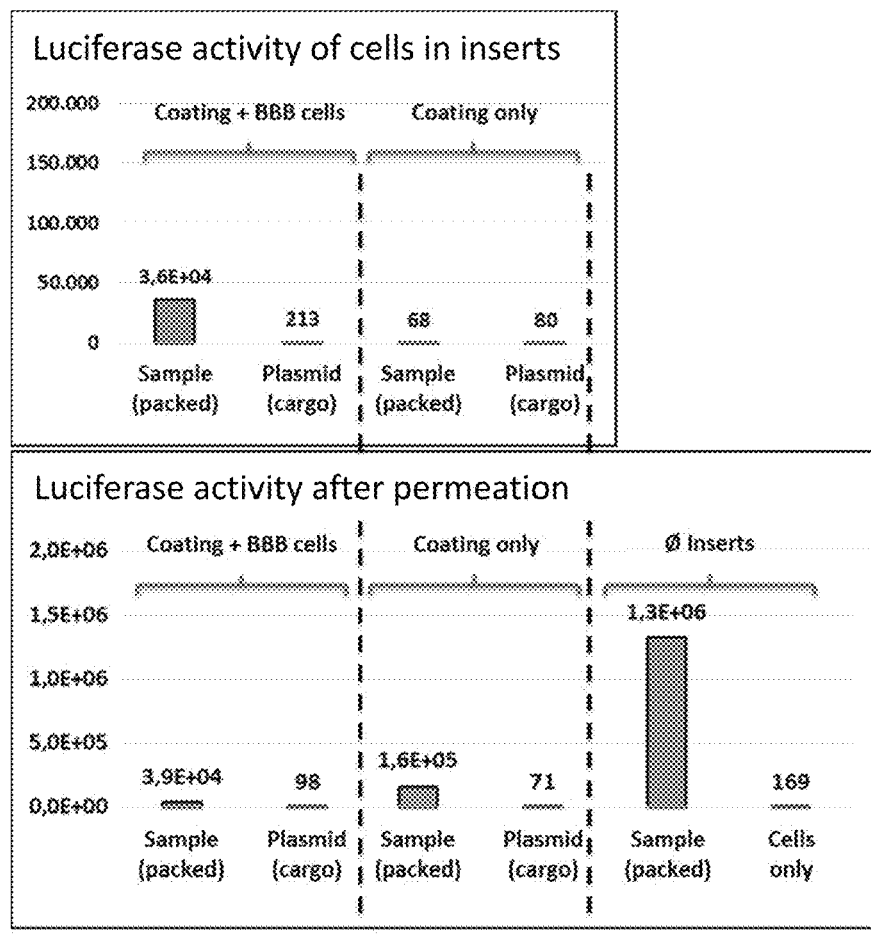

To assess the delivering efficacy of VLP generated according to the present invention into target cells a co-culture BBB model was used (FIG. 3). FIG. 3A shows the setup of an artificial BBB model for testing BBB permeation by VLP or plasmid (circles) and subsequent protein expression caused by permeated material in target cells in a co-culture setup. FIG. 3B shows the Luciferase activity that was measured in the BBB cells present in the insert (in HBEC-5i cells) and Luciferase activity in the target cells after permeation. An artificial BBB ("Coating+BBB cells") and a coating without BBB cells ("Coating only") were tested. Luciferase activity of the cells of the inserts was only measured when there were cells present (thus, the "Coating only" samples did not show any luciferase activity as expected) and when the luciferase plasmid was packed into VLP that were prepared according to the present invention (compared with plasmid only). Luciferase activity of the target cells was also only measured in the samples with the VLP prepared according to the method of the present invention (compared with plasmid only) irrespective if the BBB cell layer was present or only the coating.

Thus, VLP prepared according to the present invention are capable of efficiently passing through the BBB while retaining a high infectivity and cargo delivering capacity. Sample (packed) means VLP that underwent two rounds of disassembly and subsequent reassembly (second reassembly in the presence of a luciferase plasmid).

Example 2: Storing Pentamers vs. Storing VLP

To investigate the homogeneity and uniformity of compositions comprising loaded VLP that had undergone different storing procedures, transmission electron microscopy (TEM) was performed. VLP that were generated with one round of disassembly and subsequent reassembly (pentamers frozen, left) were compared with VLP that were generated with two rounds of disassembly and subsequent reassembly (VLP frozen, right) (FIG. 4). The VLP generated in the latter case showed a significantly more uniform distribution as they lacked any visible defective viral particle structures when compared to the VLP wherein the pentamers were frozen during manufacturing.

To further investigate the homogeneity of loaded VLP generated as in FIG. 4, FFF-MALS analyses were performed (FIG. 5). Both samples were compared with freshly prepared VLP (without cargo, thus without disassembly/reassembly), serving as reference. Strikingly, compared with the reference (FIG. 5C), VLP generated after two rounds of disassembly and subsequent reassembly with intermediate freezing of VLP (FIG. 5A) significantly reduced the amount of VLP aggregates present in the composition. In addition, the distribution of VLP was even more uniform. The size of the VLP and the presence of "Tinies" and "Salts, debris, pentamers" was comparable.

Remarkably, when VLP were generated after one round of disassembly and subsequent reassembly (pentamers frozen) very few structurally intact VLP could be identified (FIG. 5B). Therefore, the inventive method allows the intermediate storage of VLP as reassembled VLP and the generation of a highly uniform population of loaded VLP with almost no aggregates. Percentages are given excluding the aggregates.

Figure 6:
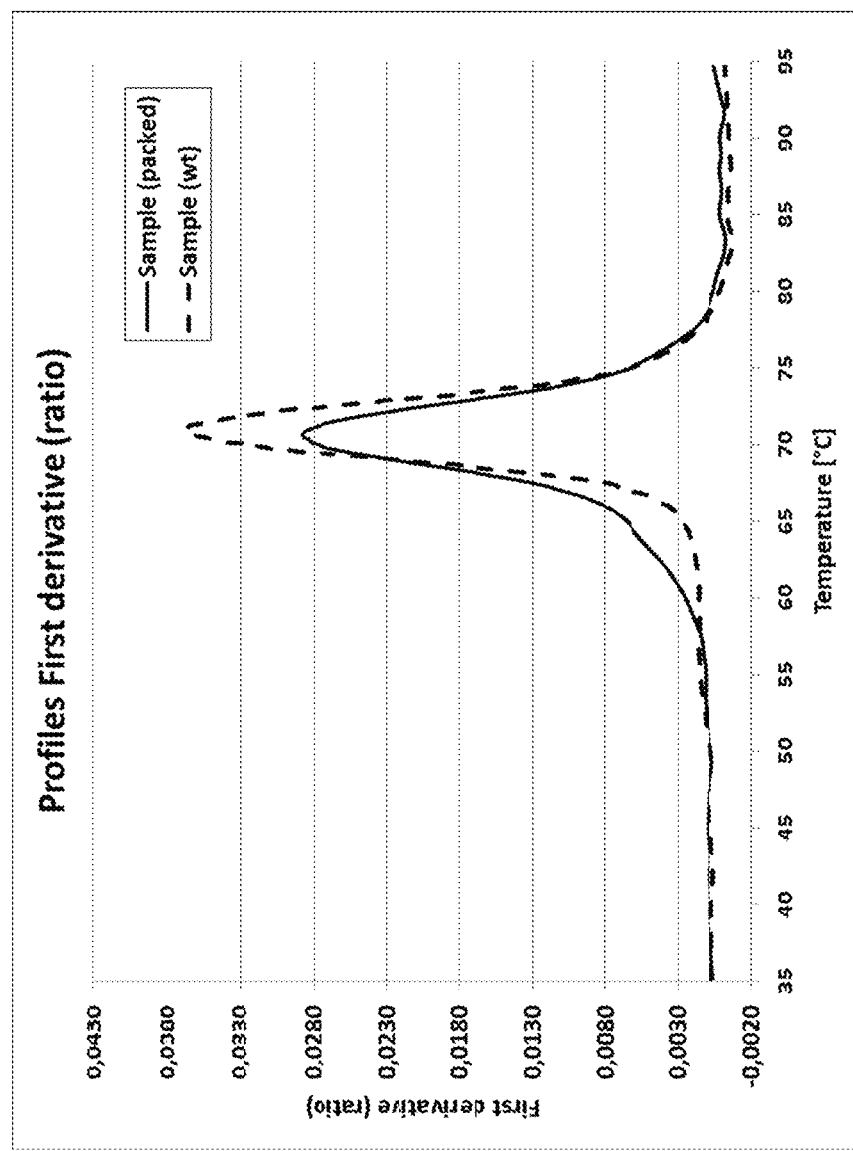
FIG. 6 nDSF analyses of freshly prepared VLP and VLP according to the invention (two rounds of disassembly and reassembly) with intermediate storage FIG. 7 DLS analyses showing the PDI of VLP according to step d) of the invention with or without inducing aggregation of pentamers before storage FIG. 8 DLS analyses showing the average diameter of VLP according to step d) of the invention with or without inducing aggregation of pentamers before storage and after storage FIGS. 9A-9B nDSF analyses (FIG. 9A) and Luciferase activity (FIG. 9B) of VLP stored with different cryoadditives

To further characterize the stability of VLP that were generated after two rounds of disassembly and subsequent reassembly with intermediate freezing of VLP ("Sample (packed)", solid line) compared with freshly prepared VLP (without cargo, thus without disassembly/reassembly, "Sample (wt)", dotted line) nDSF analyses were carried out in order to reveal melting temperatures (inflection temperatures) (FIG. 6). Remarkably, the melting curves of both VLP samples were hardly distinguishable showing that VLP prepared according to the inventive method are equally stable as freshly prepared VLP.

Example 3: Inducing Aggregation Before Reassembly

Figure 7:
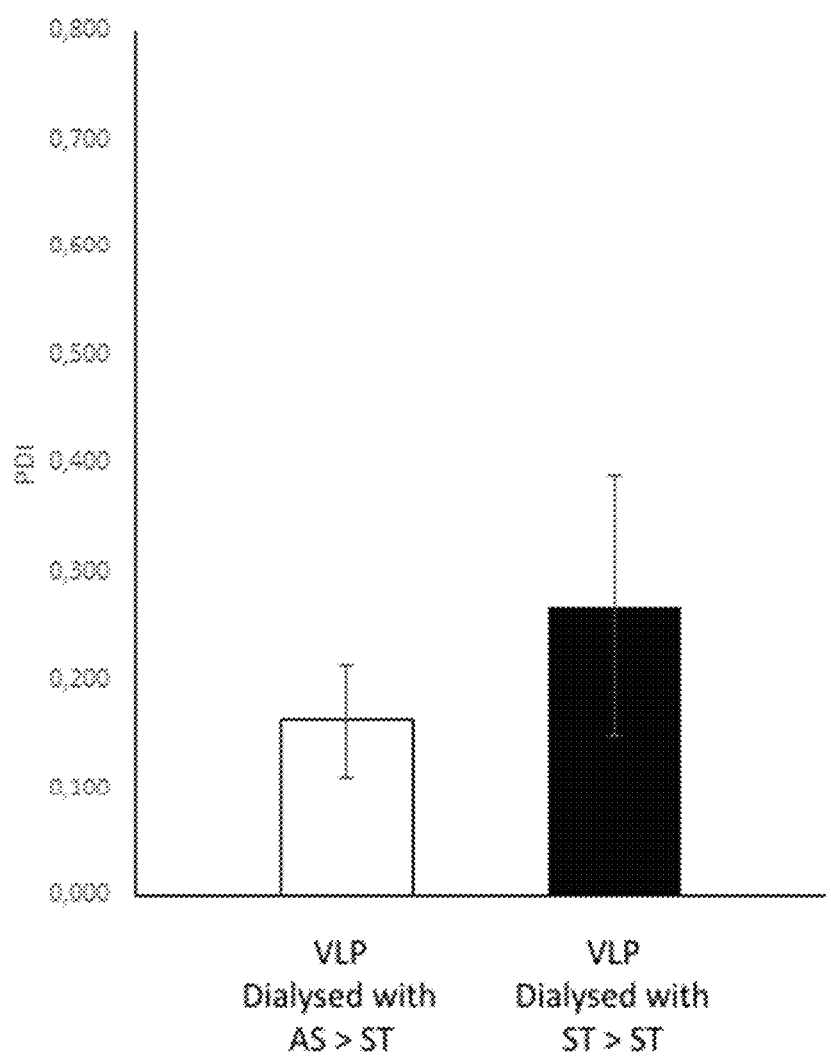
Figure 8:
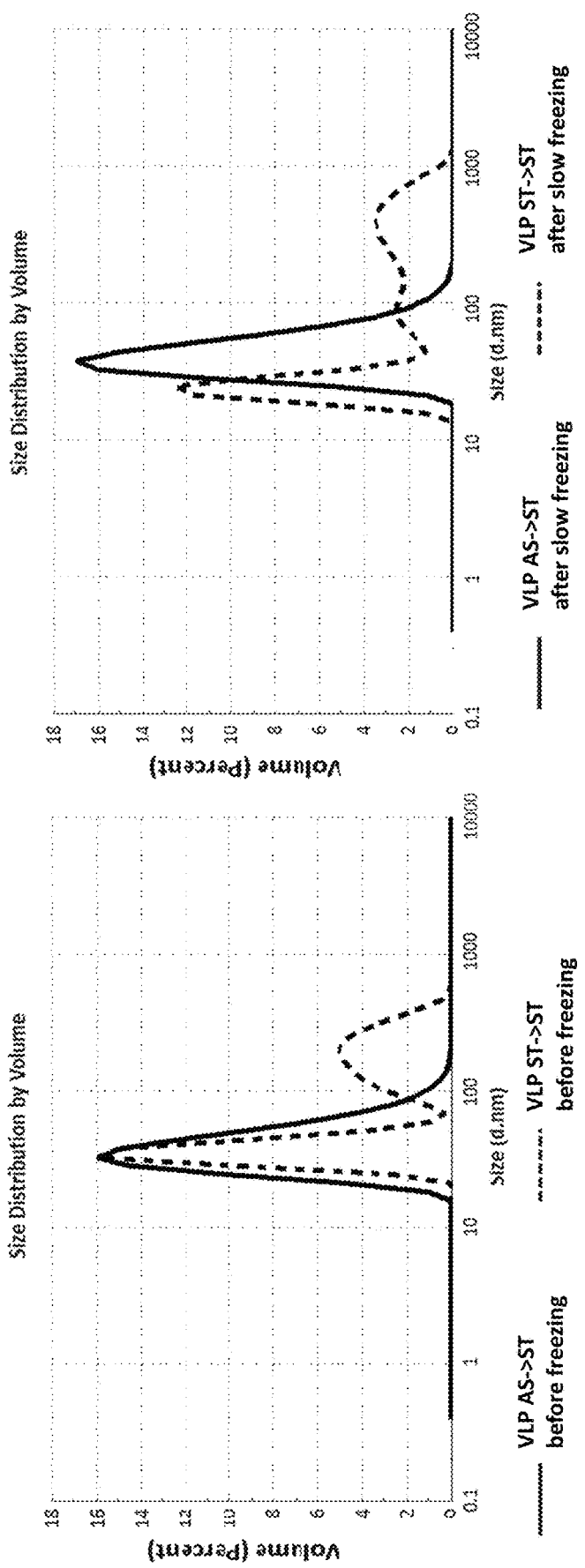

Next, the effect of inducing aggregation during reassembly of pentamers into VLP was measured. Homogeneity was analyzed by DLS (FIGS. 7 and 8). FIG. 7 shows the PDI of VLP obtained after dialysis with induction of aggregation (white column) and without induction of aggregation (black column). VLP reassembled by first inducing aggregation showed a strongly reduced PDI compared with the VLP reassembled without induction of aggregation. Therefore, the induction of aggregation during reassembly led to a much more homogenous size distribution. Both samples were taken before freezing (thus, they underwent one round of disassembly and reassembly).

FIG. 8 shows the average size distribution determined by DLS of the samples prepared as in FIG. 7 (FIG. 8, left) and samples that had undergone the same reassembly conditions but a subsequent freezing step (FIG. 8, right). Both samples that had been reassembled with induction of aggregation (solid lines) show a very uniform size distribution, while the samples that did not undergo the aggregation step (dotted lines) show at least two VLP populations. Even more, the freezing step was obviously harmful for the latter sample as the composition comprising the VLP that had been reassembled without induction of aggregation had become considerably more heterogeneous after freezing. However, the VLP that had been reassembled with induction of aggregation could be frozen without any impact on the homogeneity of the sample.

Example 4: Effect of Cryoadditives

Figure 9A:
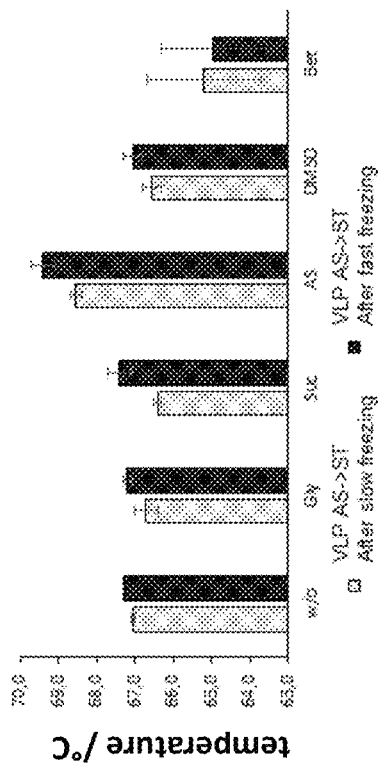

To further scrutinize the effect of sample storage on VLP, different cryoadditives were added to compositions comprising VLP that were frozen after one round of disassembly and subsequent reassembly and two dialysis steps including AS buffer (for induction of aggregation during reassembly) (FIG. 9). FIG. 9A shows the stability of loaded VLP that had been stored as depicted as analyzed by nDSF. Remarkably, VLP that had been stored in a buffer comprising ammonium sulfate were considerably more stable (i. e. show a higher inflection temperature) compared with the other cryoadditives. Interestingly, this effect was independent of whether the VLP had been frozen fast (black columns) or slowly (dotted columns).

Figure 9B:
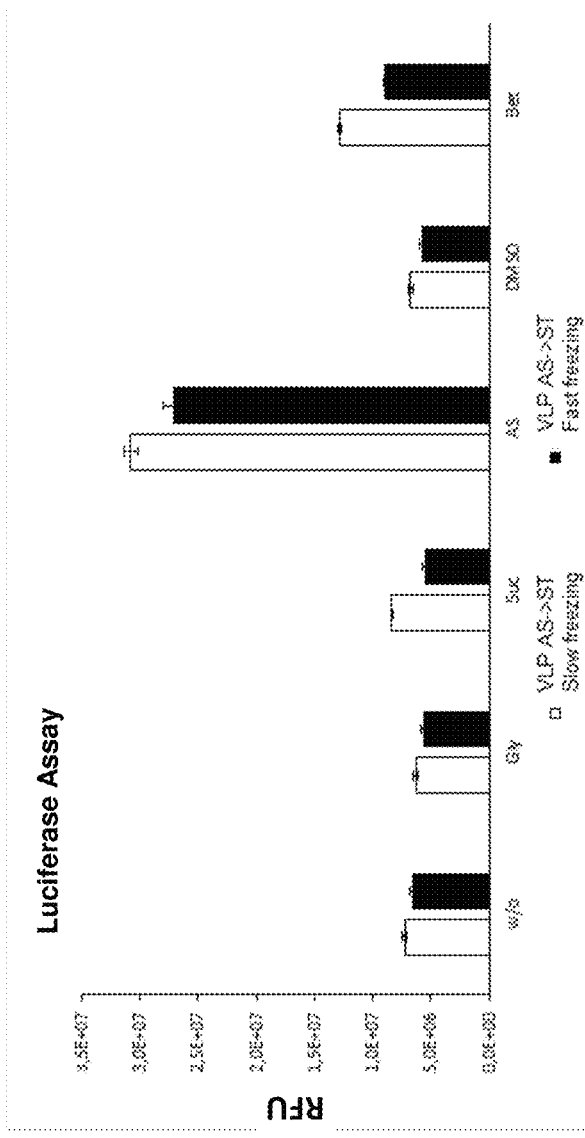

In a next step, these samples were used in a luciferase assay (FIG. 9B). Unexpectedly, the luciferase activity was strongly increased by VLP which were stored in a composition comprising ammonium sulfate. Betaine was also advantageous compared with the sample without cryoadditive and the other tested cryoadditives. Therefore, the use of cryoadditives, especially ammonium sulfate, considerably increased the stability of VLP and increased the infectivity and cargo-delivering efficacy of the loaded VLP. Again, this effect was independent of whether the VLP had been frozen fast (black columns) or slowly (white columns).

The invention claimed is:

1. A method for providing a drug delivery system comprising a virus-like particle (VLP) derived from John Cunningham virus (JCV) comprising the following steps:
   a) providing a composition comprising VP1 proteins,
   b) exposing the VP1 proteins of the composition of a) to conditions inducing the VP1 to assemble into VLP,
   c) exposing the VLP of the composition of b) to conditions disassembling the VLP into pentamers,
   d) exposing the pentamers of the composition of c) to conditions inducing the pentamers to reassemble into VLP
   e) exposing the VLP of the composition of d) to conditions disassembling the VLP into pentamers, and
   f) exposing the pentamers of the composition of e) to a cargo and conditions inducing the pentamers to assemble into a VLP associated with the cargo.

2. The method according to claim 1, wherein before step d) the pentamers of the composition of c) are exposed to conditions inducing the aggregation of the pentamers.

3. The method according to claim 2, wherein the aggregation is induced by a precipitation agent.

4. The method according to claim 3, wherein the precipitation agent is a salt comprising an anion and a cation selected from the group consisting of citrate (C6H5O73-), phosphate (PO43-), sulfate (SO42-), hydrogen phosphate (HPO42-), dihydrogen phosphate (H2PO4-), iodate (IO3-), hydroxide (OH-), fluoride (F-), bromate (BrO3-) acetate (CH3COO-), quaternary ammonium compounds (NR4+) with R being an alkyl or an aryl group, ammonium (NH4+), potassium (K+), caesium (Cs+), rubidium (Rb+), and lithium (Li+).

5. The method according to claim 3, wherein the precipitation agent is a salt, and wherein the salt is selected from the group consisting of (NH4)2SO4, K2SO4, Na2SO4, (NH4)2HPO4, K2HPO4 and Na2HPO4.

6. The method according to claim 2, wherein step d) includes separating the pentamers of composition d) from the conditions inducing the aggregation of the pentamers.

7. The method according to claim 6, wherein the separation is achieved by a dialysis against a composition comprising a salt and a buffer and a pH of 6 to 8.5.

8. The method according to claim 1, wherein the composition of step d) is characterized by
a) a polydispersity index (PDI) of less than 0.3, and/or b) at least 70% of the VLP having an average diameter of 20 nm to 70 nm.

9. The method according to claim 1, comprising a step of storing the VLP from the composition of step d) for at least 10 h at a temperature of about −80° C. to about 4° C.

10. The method according to claim 9, wherein storing takes place in a composition comprising a cryoadditive.

11. The method according to claim 10, wherein the cryoadditive is an inorganic salt and/or amino acid and/or amino acid derivative and the inorganic salt comprises a sulfate anion and/or the amino acid is glycine, glutamine, proline, or alanine and/or the amino acid derivative is betain.

12. The method according claim 1, wherein the VLP of step b), the pentamers of step c) and/or the VLP of step d) are subject to purification.

13. The method according to claim 1, wherein the VP1 comprises an amino acid sequence which is at least 80% identical to the amino acid sequence of SEQ ID NO: 1 over its entire length.

14. The method according to claim 1, wherein a nucleotide sequence encoding the VP1 protein is at least 70% identical to the nucleotide sequence of SEQ ID NO: 2 over its entire length.

15. The method according to claim 3, wherein the precipitation agent is selected from the group consisting of polyethylene glycol (PEG), alcohol, and a salt, or a combination thereof.

16. The method according to claim 3, wherein the precipitation agent is a salt.

17. The method according to claim 4, wherein the salt comprises a quaternary ammonium compound (NR4+) selected from the group consisting of tetramethylammonium ((CH3)4N+) and dimethylammonium ((CH3)2N2+).

18. The method according to claim 4, wherein the salt comprises 5042- or NH4+.

19. The method according to claim 5, wherein the salt is (NH4)2SO4.

20. The method according to claim 6, wherein the separation is achieved by a dialysis against a composition comprising a salt and a buffer and a pH of 7 to 8.

21. The method according to claim 6, wherein the separation is achieved by a dialysis against a composition comprising a salt and a buffer and a pH of 7.2 to 7.5.

22. The method according to claim 6, wherein the separation is achieved by a dialysis against a composition comprising a salt and a buffer and a pH of 7.5.

23. The method according to claim 8, wherein the composition of step d) is characterized by a polydispersity index (PDI) of less than 0.2.

24. The method according to claim 8, wherein the composition of step d) is characterized by a polydispersity index (PDI) of less than 0.1.

25. The method according to claim 8, wherein the composition of step d) is characterized by a polydispersity index (PDI) of between 0.01 and 0.09.

26. The method according to claim 8, wherein the composition of step d) is characterized by at least 70% of the VLP having an average diameter of 30 nm to 70 nm.

27. The method according to claim 8, wherein the composition of step d) is characterized by at least 70% of the VLP having an average diameter of 35 nm to 65 nm.

28. The method according to claim 8, wherein the composition of step d) is characterized by at least 70% of the VLP having an average diameter of 40 to 60 nm.

29. The method according to claim 9, wherein the step of storing the VLP from the composition of step d) is for at least 24 h.

30. The method according to claim 9, wherein the step of storing the VLP from the composition of step d) is at a temperature of about −80° C. for at least 24 h.

31. The method according to claim 10, wherein the cryoadditive is selected from the group consisting of polyols, sugars, inorganic salts, organic salts, amino acids, polymers, extremolytes, and derivatives or combinations thereof.

32. The method according to claim 11, wherein the cryoadditive is an inorganic salt, and wherein the inorganic salt is ammonium sulfate.

33. The method according to claim 13, wherein the VP1 comprises an amino acid sequence which is at least 90% identical to the amino acid sequence of SEQ ID NO: 1 over its entire length.

34. The method according to claim 13, wherein the VP1 comprises the amino acid sequence of SEQ ID NO: 1.

35. The method according to claim 14, wherein a nucleotide sequence encoding the VP1 protein is at least 80% identical to the nucleotide sequence of SEQ ID NO: 2 over its entire length.

36. The method according to claim 14, wherein a nucleotide sequence encoding the VP1 protein is at least 90% identical to the nucleotide sequence of SEQ ID NO: 2 over its entire length.

37. The method according to claim 14, wherein a nucleotide sequence encoding the VP1 protein is the nucleotide sequence of SEQ ID NO: 2.

* * * * *